(12) United States Patent
Parry-Billings et al.

(10) Patent No.: US 11,052,202 B2
(45) Date of Patent: Jul. 6, 2021

(54) DRUG DELIVERY DEVICE FOR THE TREATMENT OF PATIENTS WITH RESPIRATORY DISEASES

(71) Applicant: CHIESI FARMACEUTICI S.p.A., Parma (IT)

(72) Inventors: Mark Parry-Billings, Parma (IT); Mario Scuri, Parma (IT); Maria Chiara Taverna, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 410 days.

(21) Appl. No.: 14/069,755

(22) Filed: Nov. 1, 2013

(65) Prior Publication Data

US 2014/0158126 A1    Jun. 12, 2014

(30) Foreign Application Priority Data

Nov. 7, 2012   (EP) .................................... 12191562

(51) Int. Cl.
| | | |
|---|---|---|
| *A61M 15/00* | (2006.01) | |
| *A61M 16/00* | (2006.01) | |
| *G16H 20/10* | (2018.01) | |

(52) U.S. Cl.
CPC .... *A61M 15/0026* (2014.02); *A61M 15/0065* (2013.01); *A61M 15/0091* (2013.01); *A61M 15/0093* (2014.02); *A61M 15/0008* (2014.02); *A61M 15/0075* (2014.02); *A61M 2016/0033* (2013.01); *A61M 2202/062* (2013.01); *A61M 2202/064* (2013.01);

(Continued)

(58) Field of Classification Search
CPC .......... A61M 15/0093; A61M 16/0051; A61M 16/0003; A61M 15/0026; A61M 15/0065; A61M 15/0091; A61M 2205/52; A61M 2205/50; A61M 2205/3584; A61M 2205/3553; A61M 2016/0033; A61M 2202/062; A61M 2206/16; A61M 2202/064; A61M 15/0075; G06F 19/3481
See application file for complete search history.

(56) References Cited

U.S. PATENT DOCUMENTS 3,555,192 A * 1/1971 Hymer ................. H03G 3/3005
                                                                 381/110
5,674,860 A * 10/1997 Carling ................ A61K 9/0075
                                                                 514/171

(Continued)

FOREIGN PATENT DOCUMENTS

DE    10 2007 058112 A1    6/2009
GB    2 451 833            2/2009
(Continued)

OTHER PUBLICATIONS

European Search Report in Application No. 12191562.3 dated Apr. 9, 2013.

*Primary Examiner* — Victoria Murphy
(74) *Attorney, Agent, or Firm* — Oblon, McClelland, Maier & Neustadt, L.L.P.

(57) ABSTRACT

Drug delivery devices that include a microphone and processing circuitry that can detect operating events, such as peak inspiratory flow (PIF) and Breath Actuated Mechanism (BAM) in dry powder inhalers can be used to improve clinical trials by providing information about the way in which the inhalers under test are being used.

15 Claims, 18 Drawing Sheets

(52) U.S. Cl.
CPC ............... *A61M 2205/3375* (2013.01); *A61M 2205/3553* (2013.01); *A61M 2205/3584* (2013.01); *A61M 2205/50* (2013.01); *A61M 2205/52* (2013.01); *A61M 2206/16* (2013.01); *G16H 20/10* (2018.01)

(56) References Cited

U.S. PATENT DOCUMENTS

| | | |
|---|---|---|
| 6,152,130 A | 11/2000 | Abrams et al. |
| 2006/0185672 A1* | 8/2006 | Pinon ................ A61M 15/0065 128/203.15 |
| 2007/0017506 A1 | 1/2007 | Bell et al. |
| 2007/0240712 A1 | 10/2007 | Fleming et al. |
| 2008/0261932 A1* | 10/2008 | Chiesi .................. A61K 31/167 514/171 |
| 2009/0308387 A1* | 12/2009 | Andersen .............. A61M 15/00 128/203.15 |
| 2010/0204688 A1* | 8/2010 | Hoey ...................... A61B 18/18 606/27 |
| 2011/0262543 A1* | 10/2011 | Cocconi ............... A61K 9/0075 424/489 |
| 2012/0247235 A1 | 10/2012 | Adamo et al. |

FOREIGN PATENT DOCUMENTS

| | | | |
|---|---|---|---|
| WO | 2011/135353 | 11/2011 | |
| WO | WO 2011/135353 A1 * | 11/2011 | ............ A61M 16/00 |

\* cited by examiner

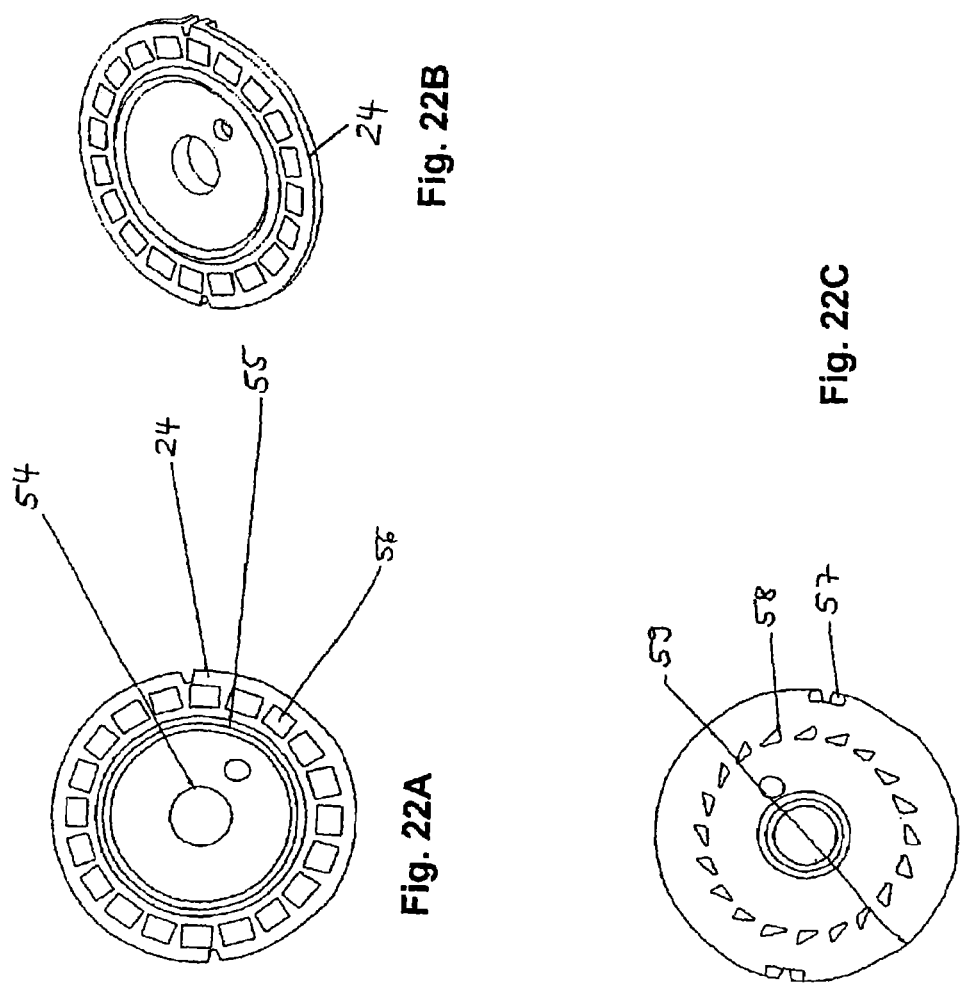

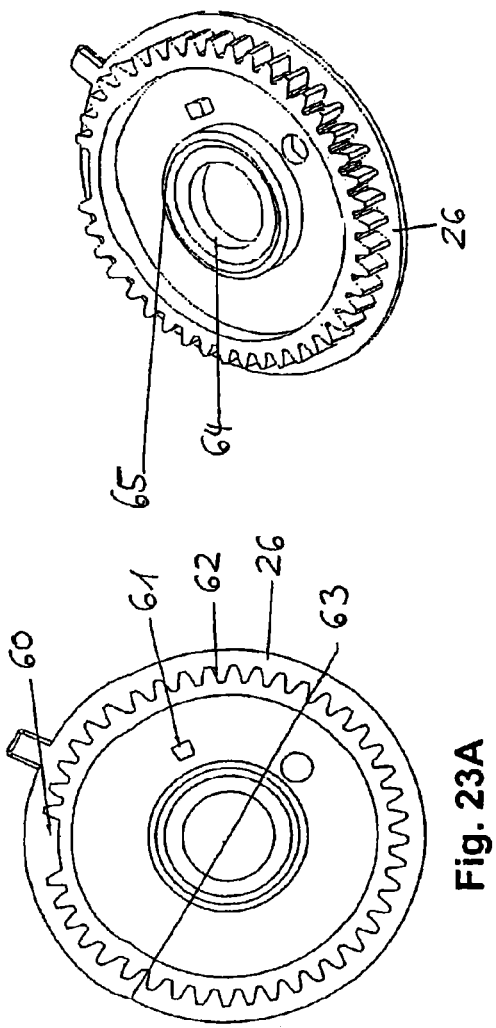
Fig. 23A
Fig. 23B
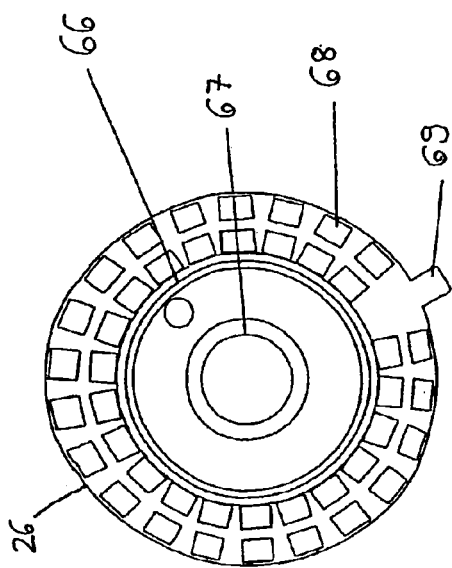
Fig. 23C

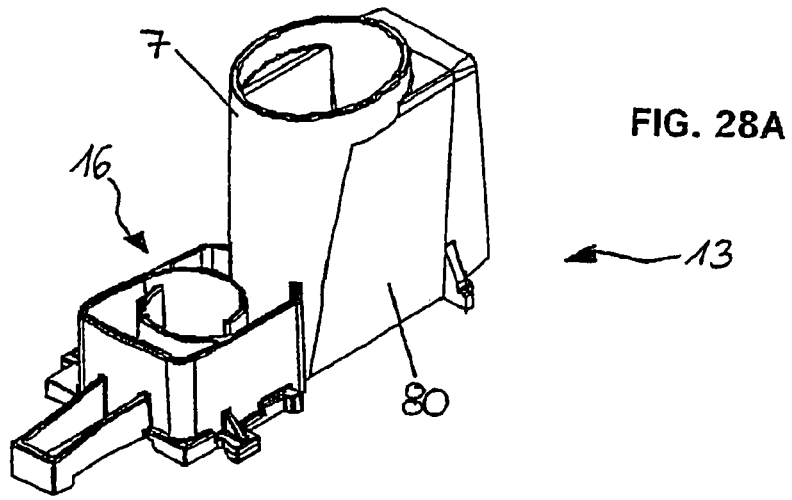
FIG. 28A
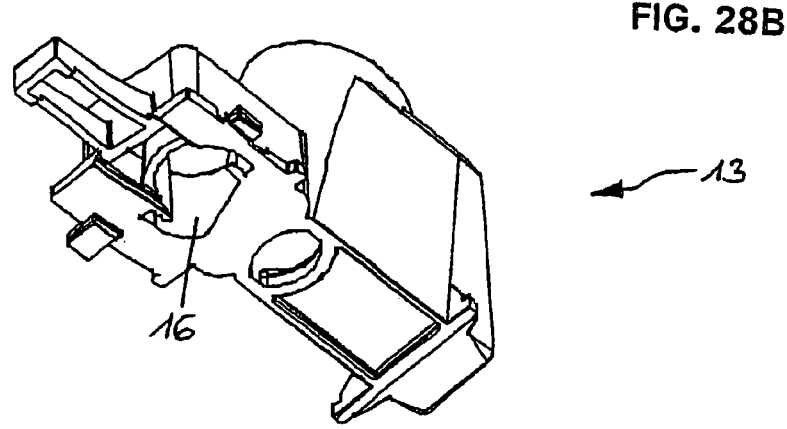
FIG. 28B
FIG. 28C
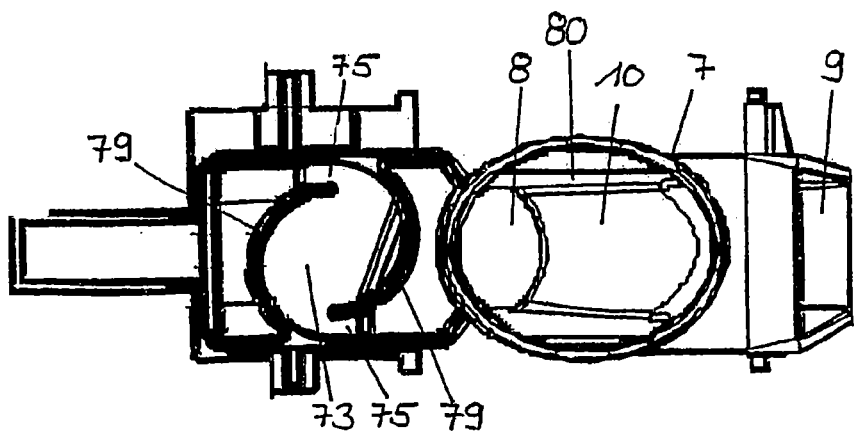

DRUG DELIVERY DEVICE FOR THE TREATMENT OF PATIENTS WITH RESPIRATORY DISEASES

CROSS REFERENCES TO RELATED APPLICATIONS

This application claims priority to European Patent Application No. 12191562.3 filed on Nov. 7, 2012, which is incorporated herein by reference in its entirety.

BACKGROUND OF THE INVENTION

Field of the Invention

The present invention relates to drug delivery devices, parts thereof, and methods of using such a device. In particular, the present invention relates to drug delivery systems comprising a dry powder inhaler (DPI), a microphone mounted on the external surface of the body of said inhaler, and a processing circuitry for use for the treatment of patients affected by respiratory diseases such as asthma or chronic obstructive pulmonary disease (COPD).

Discussion of the Background

Drugs such as beta$_2$-adrenergic agonists, steroids, and anticholinergics are widely administered by inhalation for the treatment of respiratory diseases. Presently, the most widely used systems for inhalation therapy are the pressurized metered dose inhalers (MDIs) which use a propellant to expel droplets containing the pharmaceutical product to the respiratory tract.

Dry powder inhalers (DPIs) constitute a valid alternative to MDIs for the administration of drugs to airways. The main advantages of DPIs are summarized below:

i) being breath-actuated delivery systems, they do not require co-ordination of actuation since release of the drug is dependent on the patient own inhalation; and ii) they do not contain propellants which may act as environmental hazards.

For example, EP 1 386 630, which is incorporated herein by reference in its entirety, discloses a pocket size, breath actuated, medium resistance DPI, having a body with a mouthpiece and provided with a deagglomerator system for deagglomerating the powdered drug, characterized by a vortex chamber having an opening for the supply of the powdered medicament, two air inlets for directing air tangentially into the vortex chamber, and an outlet for outputting air with the deagglomerated powdered medicament, the outlet being spaced from the air inlets in an axial direction of the deagglomerator arrangement, wherein an outer wall of each air inlet is connected to the other air inlet by an arched wall portion of the vortex chamber.

Said deagglomerator system has also been termed as cyclone.

However since DPIs rely on the force of the patient to break-up the powder into particles that are small enough to reach the lungs, insufficient patient inhalation flow rates may lead to reduced dose delivery and incomplete deaggregation of the powder, leading to unsatisfactory device performance.

It is therefore of paramount importance to understand the relationship between the inspiratory flow generated by the patient inside the device and its association with different degrees of functional limitation, and the corresponding efficiency with which the drug is dispersed and eventually inhaled into the airways.

In particular, it would be highly advantageous to provide tools for an accurate assessment of the inspiratory flow generated by the patients through the device of EP 1 386 630 and to investigate whether this maneuver results in the activation of the breath actuated mechanism (BAM) and, hence, the delivery of the intended dose in patients with respiratory diseases.

However, when the inspired air pass through the deagglomerator system of the inhaler of EP 1 386 630, it does not generate detectable vortex frequencies.

WO 2011/135353, which is incorporated herein by reference in its entirety, discloses a technology to measure/monitor key performance characteristics during the inspiratory maneuver of formulations through the air path of inhaler, such as such as dry powder inhalers, metered dose inhalers, nasal inhalers and nebulizers. However, it is silent about the application to DPIs provided with a deagglomerator system for deagglomerating the powdered drug arranged as disclosed in EP 1 386 630.

Thus, there remains a need for improved DPIs.

SUMMARY OF THE INVENTION

Accordingly, it is one object of the present invention to provide novel DPIs.

It is another object of the present invention to provide novel methods of treating respiratory diseases such as asthma or chronic obstructive pulmonary disease (COPD) by administering a drug with such a DPI.

These and other objects, which will become apparent during the following detailed description, have been achieved by the inventors' discovery that the technology disclosed in WO 2011/135353 can be applied to an inhaler and can be successfully used for monitoring/assessing its key performances in patients with respiratory diseases.

Thus, the present invention provides:

(1) A dry powder inhaler constituted of a body (1) and a cover (2), said body comprising a container (7) for storing a powdered medicament, a metering member (15) having a dosing recess (18), the metering member (15) being moveable between a filling position, in which the dosing recess (18) is in alignment with an opening of the container (7) so as to be filled with a dose of the powdered medicament, and an inhalation position, in which the dosing recess (18) is in alignment with an inhalation channel (27), a mouthpiece (3) being in communication with the inhalation channel (27) for enabling inhalation of the dose of the powdered drug contained in the dosing recess (18) of the metering member (15) when the metering member (15) is in the inhalation position, a protective member (19) provided between the metering member (15) and the inhalation channel (27), being moveable between a closed position, in which the protective member (19) at least covers the dosing recess (18) of the metering member (15) when the metering member (15) is in the inhalation position, thereby preventing the powdered medicament contained in the dosing recess (18) from entering into the inhalation channel (27) and an open position, in which the protective member (19) does not cover the dosing recess (18), thereby exposing the dosing recess (18) to the inhalation channel (27) so as to enable inhalation of the dose of the powdered medicament contained in the dosing recess (18), a breath actuated mechanism (BAM) coupled to the protective member (19) such that, if the protective member (19) is in the closed position, the BAM (21, 23) causes the protective member (19) to move into the open position if an inhalation suction force being effected by a patient exceeds a predetermined value, an inhalation cannel (27) provided with a deagglomerator arrangement (16) for deagglomerating a powdered medicament, comprising a vortex chamber (73) having an opening for the supply of the powdered medicament, two air inlets (75) for directing air tangentially into the vortex chamber (73), and an outlet (74) for outputting air with the deagglomerated powdered medicament, the outlet (74) being spaced from the air inlets (75) in an axial direction of the deagglomerator arrangement (16), wherein an outer wall of each air inlet (75) is connected to the other air inlet (75) by an arched wall portion (79) of the vortex chamber (73), each arched wall portion (79) being positioned non-concentric to a horizontal circle (77) defining a diameter (d) of the vortex chamber (73) of 6 mm≤d≤10 mm;

in combination with a microphone (90) integrated with a preamplifier (91) mounted on the external surface of the body (1) of said inhaler, and processing circuitry (95) operable to process the acoustic signal obtained from said microphone (90) to determine the operating conditions of the dry powder inhaler, for use for the treatment of patients affected by a respiratory disease.

In another embodiment, the present invention provides therapeutic methods of treating a disease or condition by administering a drug with such a dry powder inhaler.

In another embodiment, the present invention provides the use of such an inhaler in combination with a microphone (90) integrated with a preamplifier (91) mounted on the external surface of the body (1) of said inhaler, and processing circuitry (95) operable to process the acoustic signal obtained from said microphone (90) to determine the operating conditions of the dry powder inhaler in the manufacture of a device useful for the treatment of patients affected by a respiratory disease.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 22A, 22b, and 22C show a front view, a perspective view, and a rear view of a units wheel of the dose counting unit.

FIGS. 23A, 23B, and 23C show a rear view, a perspective view, and a front view of a tens wheel of the dose counting unit.

FIGS. 28A, 28B, and 28C show a perspective view, a bottom view and a top view, respectively, of a dosing sub-assembly of a powder inhaler according to a further embodiment of the invention.

DETAILED DESCRIPTION OF THE PREFERRED EMBODIMENTS

Figure 1:
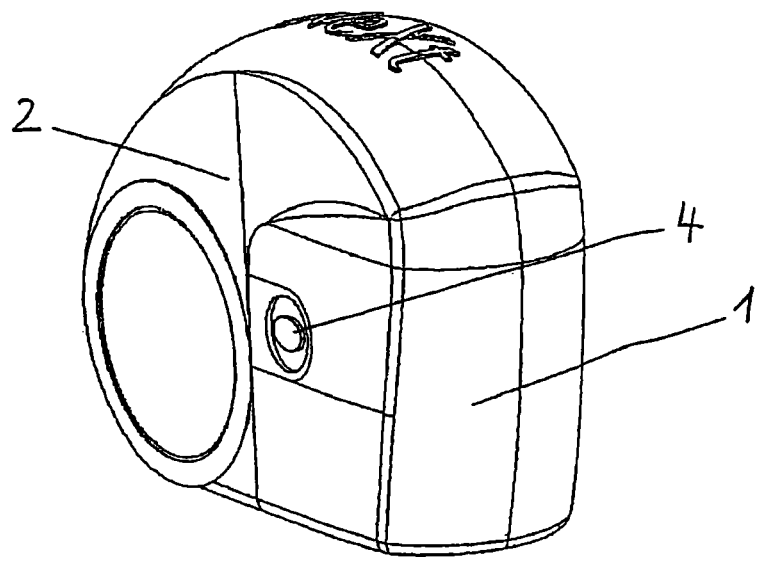
FIG. 1 shows a perspective outside view of a powder inhaler according to a preferred embodiment of the present invention.

As used herein, the term "dry powder inhaler (DPI)" refers to a device that delivers medication to the lungs in the form of a dry powder. DPIs can be divided into two basic types:

i) single dose inhalers, for the administration of pre-subdivided single doses of the active compound; and ii) multidose dry powder inhalers (MDPIs), either with pre-subdivided single doses or pre-loaded with quantities of active ingredient sufficient for multiple doses; each dose is created by a metering unit within the inhaler.

On the basis of the required inspiratory flow rates (l/min) which in turn are strictly depending on their design and mechanical features, DPI's are also divided as follows:
i) low-resistance devices (>90 l/min);
ii) medium-resistance devices (about 60-90 l/min);
iii) medium-high resistance devices (about 50-60 l/min);
iv) high-resistance devices (less than 30 l/min).

The reported classification is generated with respect to the flow rates required to produce a pressure drop of 4 KPa (KiloPascal) in accordance to the European Pharmacopoeia (Eur Ph).

The terms "body" and "casing" are used as synonymous.

The term "inspiratory flow rate by time" refers to the profile of the rate of the inspiratory flow of air, measured in volume per unit time, along the time.

The expression "the flow at and time to BAM" refers to the air flow measured at the firing (opening) of the breath actuation mechanism (BAM) and delivery of the medicament from the device and the time at which the BAM opens.

The terms "peak inspiratory flow (PIF) and time to PIF" refer to the maximum flow during inspiration of the patient through the device, and the time at which PIF occurs.

The term initial acceleration refers to the rate at which the inspiratory flow changes starting from time 0 to the BAM firing (opening).

The term "MicroElectrical-Mechanical System (MEMS) microphone" refers to a microphone chip or silicon microphone. The pressure-sensitive diaphragm is etched directly into a silicon chip by MEMS techniques, and is usually accompanied with integrated preamplifier. Most MEMS microphones are variants of the condenser microphone design. Often MEMS microphones have built in analog-to-digital converter (ADC) circuits on the same CMOS chip making the chip a digital microphone and so more readily integrated with modern digital products. Major manufacturers producing MEMS silicon microphones are Wolfson Microelectronics, Analog Devices, and Akustica Infineon, Knowles Electronics, Memstech, NXP Semiconductors, Sonion MEMS, AAC Acoustic Technologies, and Omron.

The present invention relates to the use of a dry powder inhaler in combination with a microphone 90 integrated with a preamplifier 91 mounted on the external surface of the body 1 of said inhaler, and processing circuitry 95 operable to process the acoustic signal obtained from said microphone 90 to determine the operating conditions of the dry powder inhaler for the treatment of patients affected by a respiratory disease.

Preferably, the microphone 90 is a MicroElectrical-Mechanical System (MEMS) microphone and it is mounted on the bottom of the body 1 of the inhaler.

The characteristics of the inhaler are reported in EP 1 386 630 which is incorporated herein by reference in its entirety.

Advantageously, the cover (2) of the device is rotatably coupled to the body (casing) (1) so that the cover (2) is moveable between a closed position, in which it covers the mouthpiece (3), and an open position, in which it exposes the mouthpiece (3).

Preferably, the body (1) comprises a window (4) for displaying a number of doses of the powdered medicament left in the container (7) or having been inhaled, the number of doses of the powdered medicament being counted by a dose counting unit (24-26).

More preferably, the body (1) also comprises an opening (5) for displaying a mark (38) showing if the dose of the powdered medicament contained in the dosing recess (18) of the metering member (15) is ready for inhalation, or has already been inhaled.

In a particular embodiment of the present invention, the container (7) comprises a medicament chamber (8) for storing the powdered medicament and an integral desiccant chamber (9) for storing a desiccant, the desiccant chamber (9) being separated from the medicament chamber (8) by a permeable membrane (10).

The acoustic signals are recorded using the microphone (90), then analyzed using a set of algorithms that are tailored by the skilled person for said particular inhaler according to WO 2011/135353, which is incorporated herein by reference in its entirety.

In particular, the processing circuitry 95 disclosed therein is operable to: i) track the acoustic signal received from the microphone 90 during an inhalation; ii) convert the acoustic signal into a flow inhalation profile using stored first calibration data; iii) process the signal obtained from the microphone 90 to detect the firing of the BAM and hence, the timing of the delivery of the powdered medicament during the inhalation; iv) and compare the detected timing of said delivery relative to said flow inhalation profile with stored second calibration data to determine if the delivery of the medicament meets a desired delivery condition.

The technique disclosed in WO 2011/135353 is completely non-invasive, having no effect upon the airflow or the aerosolization performance of the inhaler, and could give a positive and immediate user feedback to the user.

Analysis of the acoustic signal produced by airflow through the DPI enables very accurate and reproducible determination of important operating conditions of the aforementioned dry powder inhaler comprising the inspiratory flow rate by time and the flow at and time to BAM, the peak inspiratory flow (PIF) and time to PIF, and total inhaled air volume.

This enables four salient scenarios to be monitored with confidence: i) flow rate profile, ii) BAM did not fire, iv) BAM fired but nothing was delivered and v) BAM fired and medicament was delivered.

Therefore, as a matter of fact, said technology allows one to establish whether the delivery of the intended dose in patients with respiratory diseases has occurred.

In another embodiment, the processing circuitry detecting the operating conditions of the inhaler is mounted within the body of the inhaler.

In an alternative embodiment, the processing may be performed by a remote processing device. In such an embodiment, the inhaler would record the signals obtained from the microphone and the data stored in the inhaler would then be downloaded to a computer device to perform the processing.

In the above embodiments, the processing circuitry 95 is able to process the signal obtained from the microphone 90 and detect if the delivery mechanism is activated during the inhalation and, if it is, to detect if the drug is also delivered by the mechanism. The processing circuitry 95 may maintain a count of the number of times that the delivery device is activated and the drug is successfully delivered and the number of times that the delivery device is activated but no drug is delivered. This information may be useful for subsequent diagnosis by the clinician or physician. Additionally, real time feedback may also be provided to the user so that they know if the drug was actually delivered. Very often with inhaler devices, users take too much of the drug because they do not realize that the drug is dispensed during one or more of their inhalations.

Advantageously, the powdered medicament filled in the inhaler is in the form of powder formulation comprising coarse carrier particles of a physiologically acceptable excipient, and micronized particles of one or more active ingredients currently utilized for the treatment of respiratory diseases.

The coarse carrier particles may have a mass median diameter (MMD) higher than 90 microns, and preferably the mass diameter (MD) is 50 microns to 500 microns, more preferably 150 to 400 microns, even more preferably 210 to 355 microns.

The coarse carrier particles have preferably a relatively highly fissured surface, that is, on which there are clefts and valleys and other recessed regions, referred to herein collectively as fissures.

The "relatively highly fissured" surface of the coarse carrier particles may be defined in terms of fissure index or rugosity coefficients as disclosed in WO 01/78695 and WO 01/78693, both of which are incorporated herein by reference in their entireties, and they can be characterized according to the description therein reported.

Preferably the powder formulation may further comprises a fraction of microparticles having a MMD lower than 35 microns composed of particles of a physiologically acceptable excipient and an additive material selected from the class of the anti-adherents such as the amino acids leucine and isoleucine or of the lubricants such as magnesium stearate, sodium stearyl fumarate stearyl alcohol, stearic acid and sucrose monopalmitate.

More preferably the powder formulation comprises a fraction of microparticles having a MMD lower than 15 microns, preferably lower than 10 microns, composed of particles of a physiologically acceptable excipient and particles of magnesium stearate according to the teaching of EP 1 274 406, which is incorporated herein by reference.

The physiologically acceptable excipient may be constituted of any amorphous or crystalline physiologically acceptable inert material of animal or vegetal source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol may also be used. The most preferred material is α-lactose monohydrate.

Examples of commercial lactose are Capsulac® and Pharmatose®. An example of commercial mannitol is Pearlitol®.

In a preferred embodiment, the fraction of microparticles is composed of 98% by weight of α-lactose monohydrate and 2% by weight of magnesium stearate and the ratio between the fraction of microparticles and the fraction of coarse particles made of α-lactose monohydrate particles is 10:90% by weight, respectively.

The amount of magnesium stearate in the final formulation is advantageously comprised between 0.02% and 1.0% by weight, preferably between 0.05 and 0.5% by weight, more preferably between 0.1 and 0.4% by weight on the total weight of the formulation.

The active ingredient may be practically any pharmaceutically active compound which can be administered by inhalation as dry powder for the treatment of respiratory diseases.

As an example, they may be chosen from short-acting and long-acting beta$_2$-agonists such as terbutalin, reproterol, salbutamol, salmeterol, formoterol, milveterol, indacaterol, olodaterol, fenoterol, clenbuterol, bambuterol, broxaterol, epinephrine, isoprenaline or hexoprenaline or salts and/or solvate forms thereof; short-acting and long-acting anticholinergics such as tiotropium, ipratropium, oxitropium, oxybutynin, aclidinium, trospium, or other compounds known with the codes GSK 573719 and GSK 1160274, in form of salts and/or solvate forms thereof; bifunctional Muscarinic Antagonist-beta2 Agonist (MABA) such as GSK 961081; corticosteroids such as butixocart, rofleponide, flunisolide, budesonide, ciclesonide, mometasone and its ester, i.e. furoate, fluticasone and its ester, i.e. propionate and furoate, beclomethasone and its ester, i.e. propionate, loteprednol or triamcinolone acetonide and solvate forms thereof; phosphodiesterase-inhibitors such as filaminast, piclamilast or roflumilast.

Formulations comprising a beta$_2$-agonist and/or an anticholinergic or a corticosteroid for inhalation, alone or in any combination thereof, constitute particular embodiments of the invention.

An even more preferred embodiment of the invention concerns formulations comprising formoterol fumarate dihydrate and beclometasone dipropionate.

Patients who may benefit from the combined use of the present invention are those, of any sex and/or age, affected by mild, moderate or severe, acute or chronic, controlled or uncontrolled, symptoms of an inflammatory or obstructive respiratory disease such as asthma and chronic obstructive pulmonary disease (COPD).

The patients who may preferably benefit of the combined use of the present invention are those affected by moderate to severe persistent asthma, as defined in the Global INitiative for Asthma (GINA) guidelines, or affected by severe COPD as defined is the Global initiative for chronic Obstructive Pulmonary Disease (GOLD) guidelines.

In fact, said patients would have a more compromised lung function, with more limited inspiratory flow, and hence they might incur in a higher risk that the delivery of the medicament does not meet the desired delivery condition.

Another sub-population of patients that may preferably benefit of the combined use of the present invention is the pediatric one, i.e. children younger than 12 years, which have an inherent limited inspiratory flow.

In one embodiment, the dry powder inhaler is one as described in U.S. Pat. No. 7,107,988, which is incorporated herein by reference in its entirety, and depicted in FIGS. 1-28.

The powder inhaler shown in FIG. 1 comprises a casing with a lower shell (body) 1 and an integral cover 2 being pivotably or rotatably coupled to the lower shell 1. In a side surface of the lower shell 1 a window 4 is formed for displaying numbers of a dose counting unit which will be described later.

Figure 2:
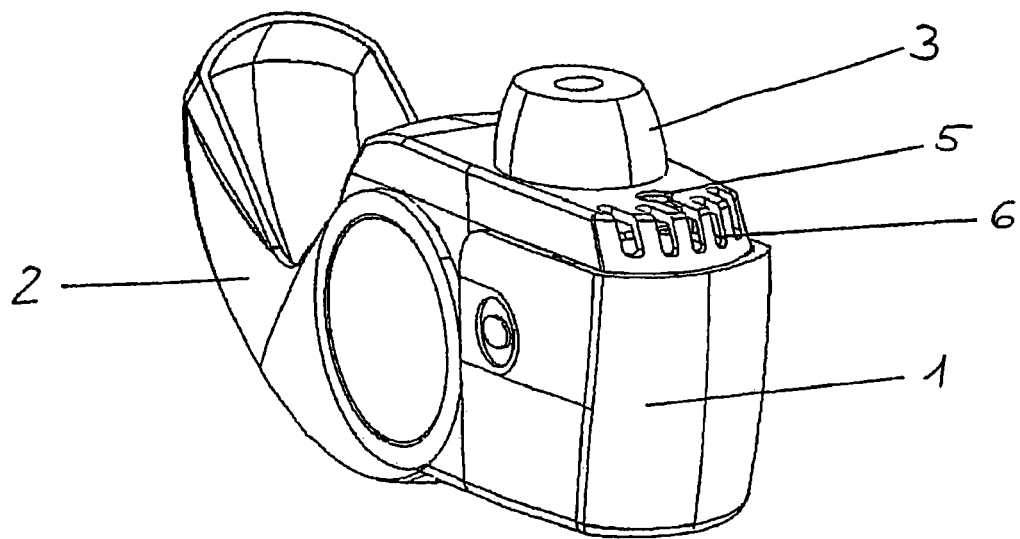
FIG. 2 shows a perspective view of the powder inhaler when a cover thereof is opened.

As can be taken from FIG. 2, the integral cover 2 can be opened to reveal a mouthpiece 3 with which a user can inhale a powdered medicament. At the upper front side of the mouthpiece 3 slots 6 are formed which allow air inlet. Furthermore, at the upper side of the mouthpiece 3 an opening or a hole 5 is formed which allows to view a visible mark or flag showing if a dose is ready. As will be described later, this flag disappears upon inhalation showing that the respective dose has been taken.

Figure 3:
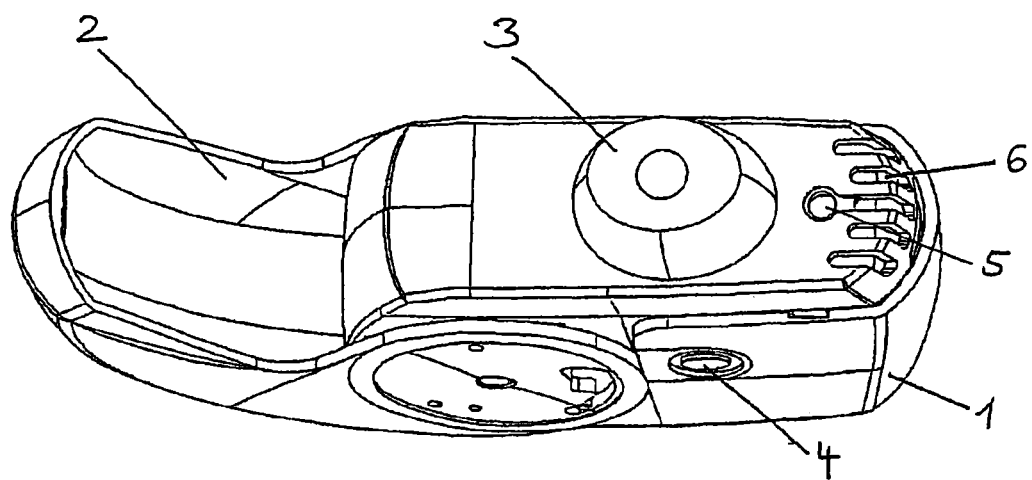
FIG. 3 shows a top view of the powder inhaler when the cover is opened.

The structure of the lower shell 1, the integral cover 2 and the mouthpiece 3 can also be taken from FIG. 3 which shows a top view of the powder inhaler. In FIG. 3 (and in FIG. 8), the integral cover 2 is shown without side labels which are depicted in FIGS. 1 and 2. These side labels prevent access to profiled cam tracks being described later so as to protect these cam tracks from dust etc.

Figure 13:
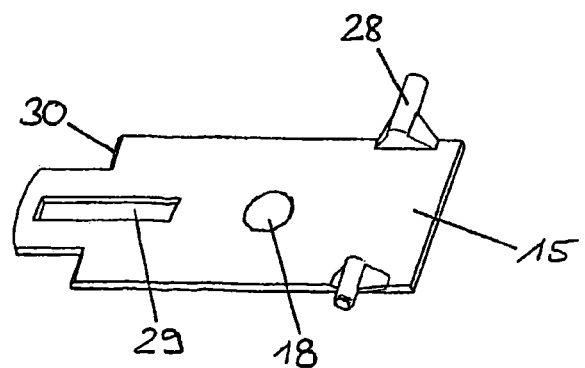
FIG. 13 shows a perspective view of a slide of the powder inhaler.
Figure 14:
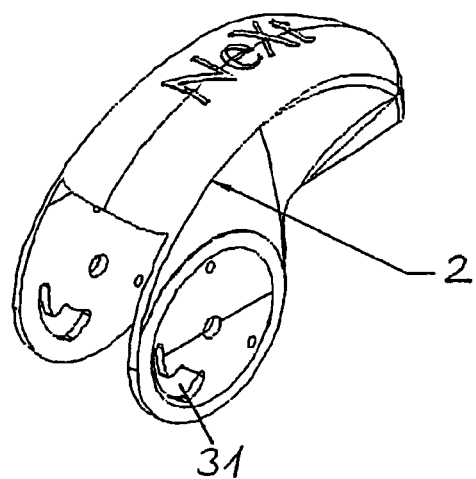
FIG. 14 shows a perspective view of the cover of the powder inhaler.
Figure 15:
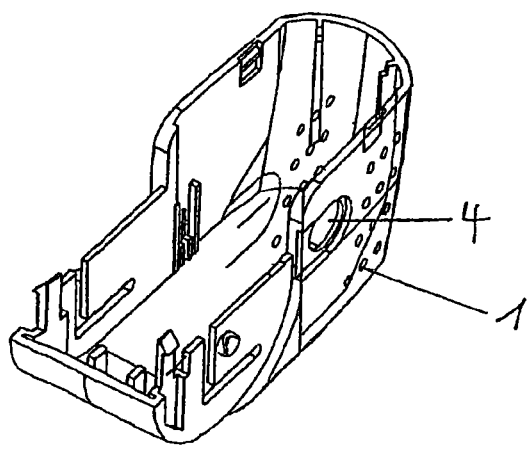
FIG. 15 shows a perspective view of a part of a casing of the powder inhaler.
Figure 16:
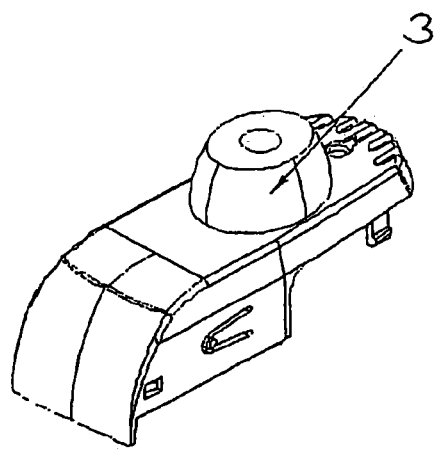
FIG. 16 shows a perspective view of a mouthpiece of the powder inhaler.

FIG. 14, FIG. 15, and FIG. 16 show perspective views of the integral cover 2, the lower shell 1, and the mouthpiece 3, respectively. The lower shell 1 and the mouthpiece 3 are constructed such that the mouthpiece 3 can be snap-fitted onto the lower shell 1. From both side surfaces of the lower shell 1 projections or bolts extend which engage with respective central openings at both side surfaces of the integral cover 2, thereby allowing rotational movement of the integral cover 2 relative to the lower shell 1. As can be seen from FIG. 1 and FIG. 2, the integral cover 2 is closed when its lower surface rests on the upper rim of the lower shell 1, and the integral cover 2 can be opened until its rear edge abuts against the underside of the lower shell 1 (see FIG. 2). At both side surfaces of the integral cover 2, openings 31 having the shape of profiled cam tracks are formed which are coupled to side projections 28 of a shuttle or slide 15, a perspective view thereof being shown in FIG. 13. This kind of coupling between the integral cover 2 and the slide 15 will be described later in detail.

Within the casing and the lower shell 1, respectively, there are two sub-assemblies arranged. The first sub-assembly is a dosing sub-assembly 13 which in particular meters a powdered medicament, while the second sub-assembly is a dose counting sub-assembly 14 which comprises an inhalation actuated mechanism and a dose counting unit for counting the number of doses taken by the user.

Figure 4:
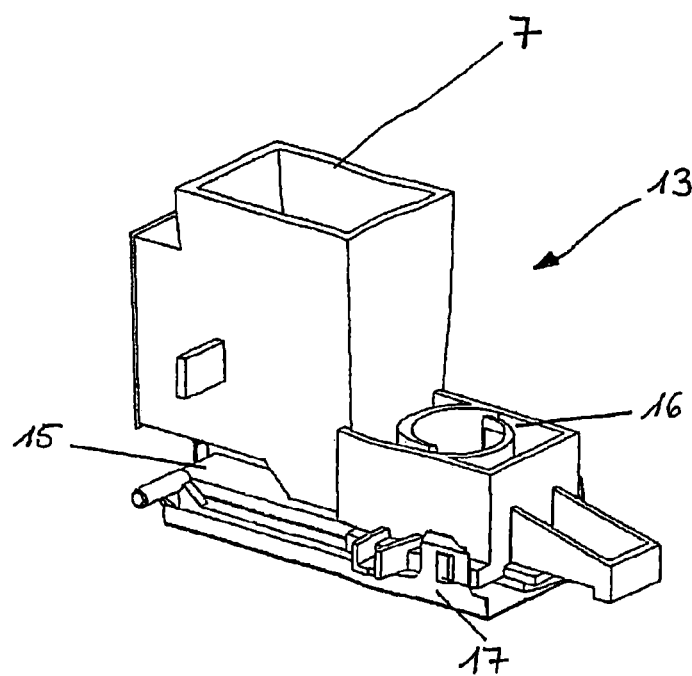
FIG. 4 shows a perspective view of a dosing sub-assembly of the powder inhaler.

FIG. 4 shows a perspective view of the dosing sub-assembly 13. As can be seen, the dosing sub-assembly 13 comprises a container or a reservoir 7 for storing a powdered medicament, the above-mentioned slide 15 shown in FIG. 13, and a deagglomerator arrangement 16 to be coupled to an inhalation channel of the mouthpiece 3. A spring 17 is clamped onto side projections of the dosing sub-assembly 13 such that it holds the dosing sub-assembly together.

Figure 18:
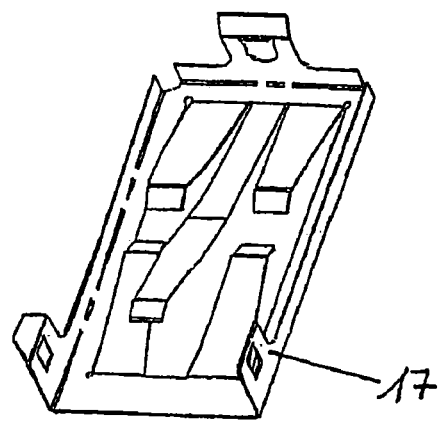
FIG. 18 shows a perspective view of a slide spring of the powder inhaler.

FIG. 18 shows a perspective view of the spring 17. As can be easily seen, the spring 17 comprises four resilient side spring members, two spring members being fixed to the rear side and two spring members being fixed to the front side of the spring 17. All four spring members extend in the longitudinal direction of the spring 17 such that their free ends are arranged in a middle portion of the spring 17. These spring members apply a force to the slide 15 such that the slide 15 is continuously urged against the underside of the dosing sub-assembly 13. From the rear side to the front side of the spring 17, there extends an additional resilient spring member which applies a separate force to the longitudinal middle region of the slide 15. As is shown in FIG. 13, in this longitudinal middle region the slide 15 has a dosing recess 18 in the form of a dosing cup for metering a dose of the powdered medicament and for transporting the dose from a filling position underneath the container 7 to an inhalation position underneath the deagglomerator arrangement 16. The above-mentioned separate spring member extending along the longitudinal middle region of the spring 17 ensures that the dosing recess 18 is reliably pressed against the underside of the dosing sub-assembly 13 if the slide 15 is in its inhalation position so that the dosing recess 18 is properly located under the deagglomerator arrangement 16.

Figures 6A, 6B:
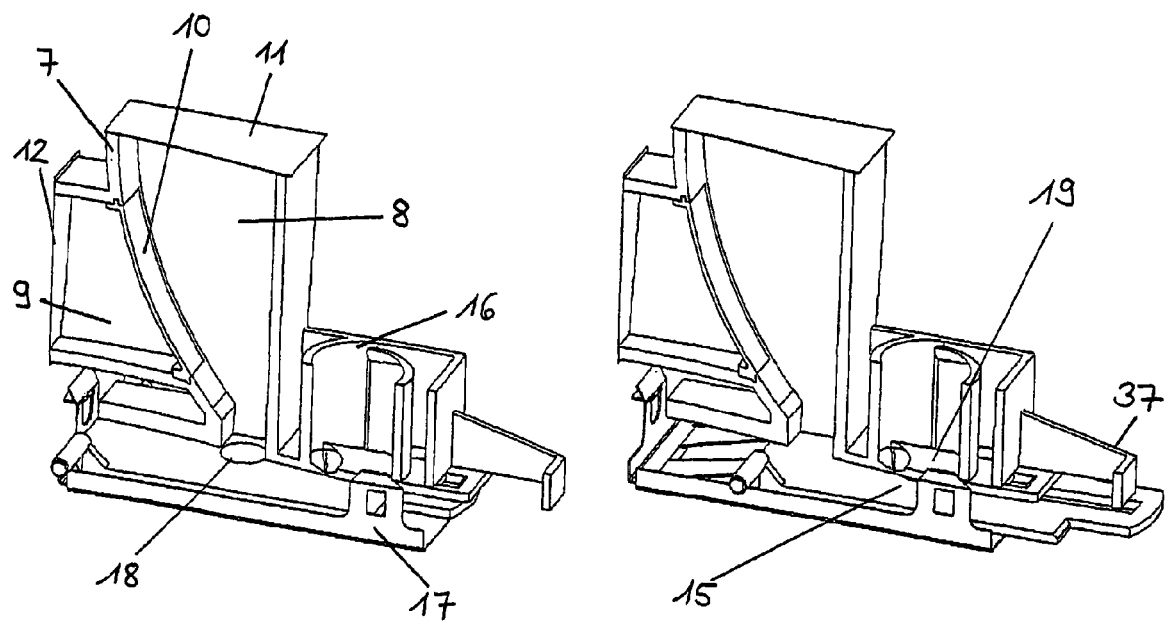
FIGS. 6A and 6B show cross-sectional views of the dosing sub-assembly.

As already indicated above, the slide 15 serves as a metering member which can be moved in the horizontal direction from a filling position shown in FIG. 6A to an inhalation position shown in FIG. 6B. Thus, the slide 15 is slidingly moveable between the filling position, where the dosing recess 18 is located underneath a dosing opening of the container 7 and faces the dosing opening, and the inhalation position, where the dosing recess 18 is located underneath and faces an inhalation opening of the deagglomerator arrangement 16 which is in communication with an inhalation channel (to be described later) of the mouthpiece 3.

As is shown in FIG. 6A, the container 7 is a container with integral desiccant. The container 7 comprises a medicament chamber 8 storing a powdered medicament and a desiccant chamber 9 storing a desiccant for absorbing moisture that may have entered the medicament chamber 8. The desiccant chamber 9 is separated from the medicament chamber 8 by a separate permeable membrane 10. This permeable membrane 10 is of a different permeability than the permeability between either the desiccant or the medicament to the outside world. The permeability of the membrane 10 can be achieved, for example, by making it of a different material and/or a thinner section than the main body of the container 7. Foils 11, 12 are used to seal both the medicament chamber 8 and the desiccant chamber 9. As a matter of course, other suitable sealing means may be used for sealing both chambers 8, 9 as well.

The above described integral desiccant system has the following advantages. The desiccant has only to dry out the medicament chamber rather than the whole device. This requires less desiccant reducing product size and cost. Furthermore, the desiccant is always sealed. This means that the desiccant will still be effective even if the cover is left open. The desiccant is stored in the separate sealed desiccant chamber 9. This reduces the risk of incorrect assembly if the desiccant used the same closure as the medicament. Moreover, the integral container 7 comprising both the medicament chamber 8 and the desiccant chamber 9 can be manufactured using a 2-shot moulding. This ensures a good seal between the medicament chamber 8 and the desiccant chamber 9 at low product cost. Finally, the foil sealing provides a tamper-proof means of filling the device with the medicament or drug which has a very low permeability and requires only little product space.

As is shown in FIG. 6A and FIG. 6B, the medicament chamber 8 has a gradually decreasing cross-section diameter from its top to its bottom so that the medicament chamber 8 is shaped like a funnel supporting an easier filling of the dosing recess 18 through the dosing opening formed in the bottom of the medicament chamber 8. The powder inhaler shown in the drawings solves many technical problems that may occur throughout the life cycle of the powder inhaler. The fundamental operating sequence of the powder inhaler is to open the integral cover 2, inhale the dose of the powdered medicament, and close the integral cover 2.

The cover 2 is gripped by the user and opened. As already described above, the projections 28 formed at both longitudinal sides of the slide 15 (see FIG. 13) engage with the respective side openings 31 formed at both sides of the cover 2. In particular, these side openings 31 are profiled cam tracks. The coupling between the profiled cam tracks 31 and the projections 28 is such that opening of the cover 2 causes the slide 15 to move forward from its filling position (FIG. 6A) to its inhalation position (FIG. 6B). Likewise, closing of the cover 2 causes the slide to move from its inhalation position backward to its filling position again. That is to say, by opening/closing the cover 2, the slide 15 is moved substantially linearly with respect to the casing. In particular, the profiled cam tracks 31 are shaped such that opening of the cover 2 by a predetermined first angle, for example, by an angle of about 30°, from its closed position does not actuate the slide 15. That is the first 30° of the movement of the cover 2 is slack where no mechanism is driven. The industrial design of the powder inhaler is intended to convey the correct orientation of use. Furthermore, the coupling between the cover 2 and the slide 15 is such that the slide 15 is properly moved to its inhalation position already a predetermined second angle, prior to the cover 2 being fully opened. For example, the slide 15 may be moved to its inhalation position already when the cover 2 has been opened by 90°. In a range of 90° 135°, e.g., there is again free play. Therefore, the dose of the powdered medicament filled in the dosing recess 18 is correctly presented to the deagglomerator arrangement 16 as well as the respective inhalation channel coupled thereto, ready for inhaling, 90° 45° prior to the cover 2 being fully open (An opening angle of 180° is considered as representing a fully open position of the cover). This ensures that the dose will be ready prior to the mouthpiece 3 becoming exposed to the user if the user should attempt a discrete operation of the powder inhaler, for example. There is an audible click indicating that the cover 2 is fully open.

When the cover 2 is closed, there are for example 45° of free play before a further closing of the cover 2 moves the slide 15 from the inhalation position to the filling position. Before the cover 2 is completely closed, there may be 15° of free play, for example. It should be noted that the profiled cam tracks 31 shown in the drawings are only exemplary.

As already mentioned before, the dosing recess 18 has the shape of a dosing cup which is designed to maximize the accuracy of gravitationally filling the dosing cup and maximize the ease of airborne entrainment of the formulation upon inhalation. The dosing cup is circular in profile (in top view) with a semi-elliptical cross-section (i.e. the cross-section has the shape of the half of an ellipse); the diameter being three times the depth. This enables the cyclonic airflow in the airway of the deagglomerator arrangement 16 to scour the dosing cup 18 effectively. The circular profile and the above-mentioned ratio of depth to top area also combine the lowest variability of filling and scraping upon leaving the container 7.

During opening the slide 15 is moved from the filling position to the inhalation position as well as after the slide 15 has reached its inhalation position, the dose of the powdered medicament filled in the dosing recess 18 of the slide 15 is prevented from falling out by a protective member, i.e. a dose protector 19. The dose protector 19 is arranged slidingly moveable on the slide 15 between a closed position and an open position. In its closed position, the dose protector 19 at least completely covers the dosing recess 18 when the slide 15 is in the inhalation position; while in its open position the dose protector 19 exposes the dosing recess 18 to the deagglomerator arrangement 16 and the inhalation channel when the slide 15 is in its inhalation position. The dose protector 19 is held in its closed position by an inhalation or breath actuated mechanism which will be described later. This inhalation actuated mechanism is constructed such that the dose protector 19 is moved from its closed position to its open position only if the inhalation suction force affected by the user in the inhalation channel exceeds a predetermined level. Furthermore, the inhalation actuated mechanism is arranged such that only an inhalation suction breath not a blowing breath can actuate the inhalation actuated mechanism and cause a movement from the dose protector from its closed position to its open position.

In the following, the inhalation actuated mechanism in combination with the dose protector and the dose counting unit is described in detail.

Figures 5A, 5B:
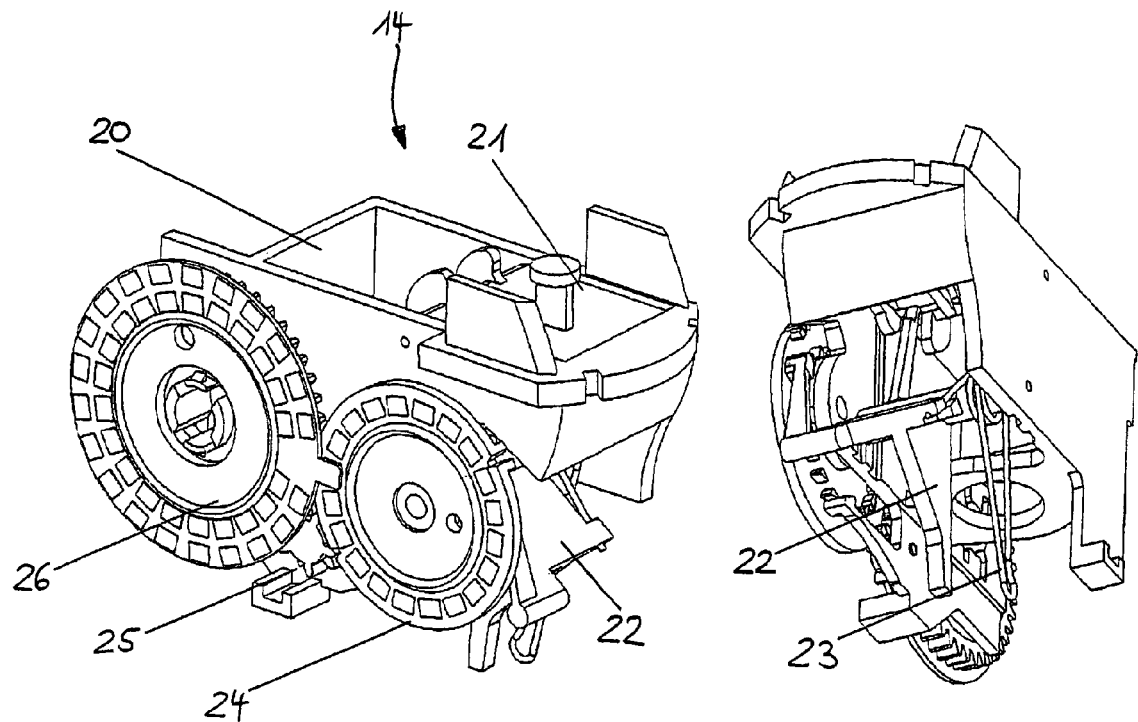
FIGS. 5A and 5B show perspective views of a dose counting sub-assembly of the powder inhaler.

FIG. 5A and FIG. 5B show perspective views of the dose counting sub-assembly 14 already mentioned above. The dose counting sub-assembly 14 consists of a sub-frame 20 which holds a flap 21 acting as an inhalation actuated member, a yoke 22 acting as a coupling member and a drive spring 23 acting as a resilient member. The drive spring 23 drives the dose counting unit which, in the present case, comprises a units wheel 24 and a tens wheel 26 being coupled by an idler wheel 25. Furthermore, the drive spring 23 drives the dose protector 19. The units wheel 24 and the tens wheel 26 display the number of doses remaining in the medicament chamber 8. As a matter of course, the drive spring 23 may be replaced with a resilient means being constituted by a plurality of spring elements or spring parts, for example.

Figures 7A, 7B:
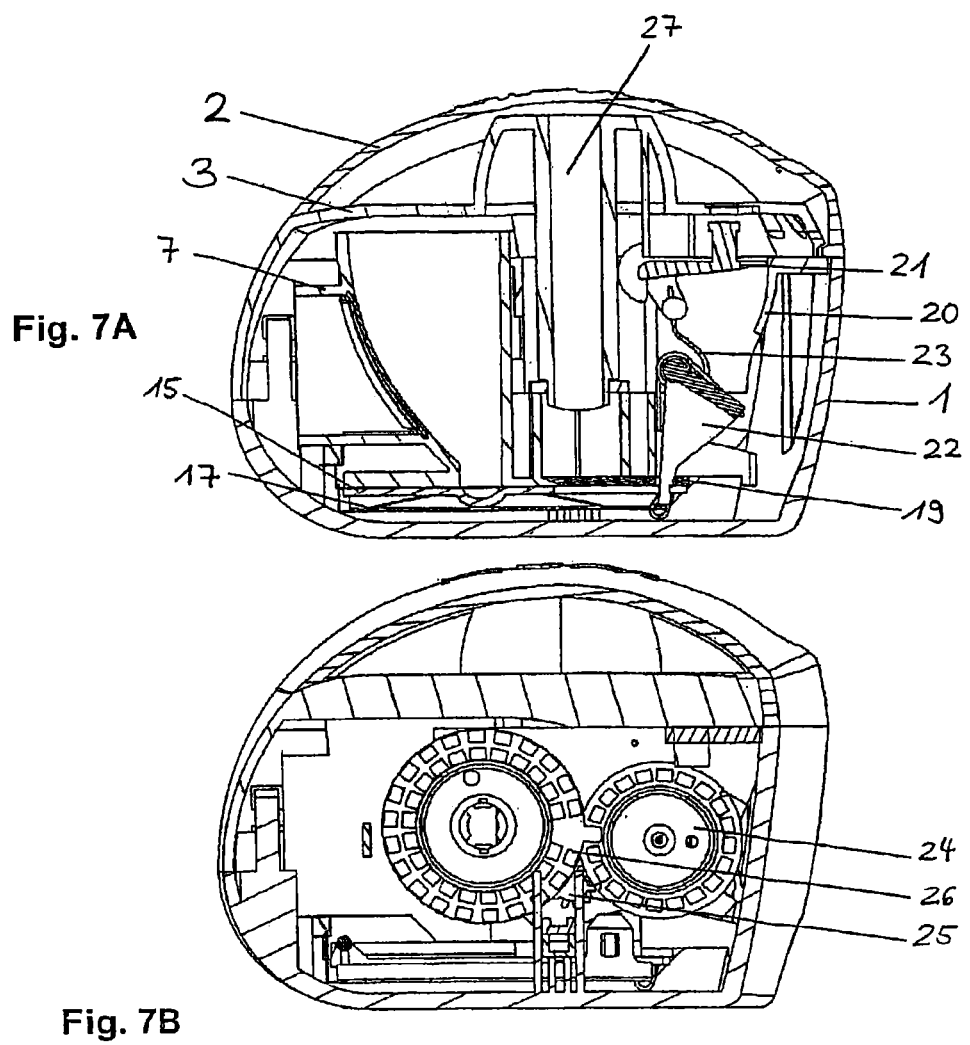
FIGS. 7A and 7B show cross-sectional side views of the powder inhaler when the cover is closed.
Figure 8:
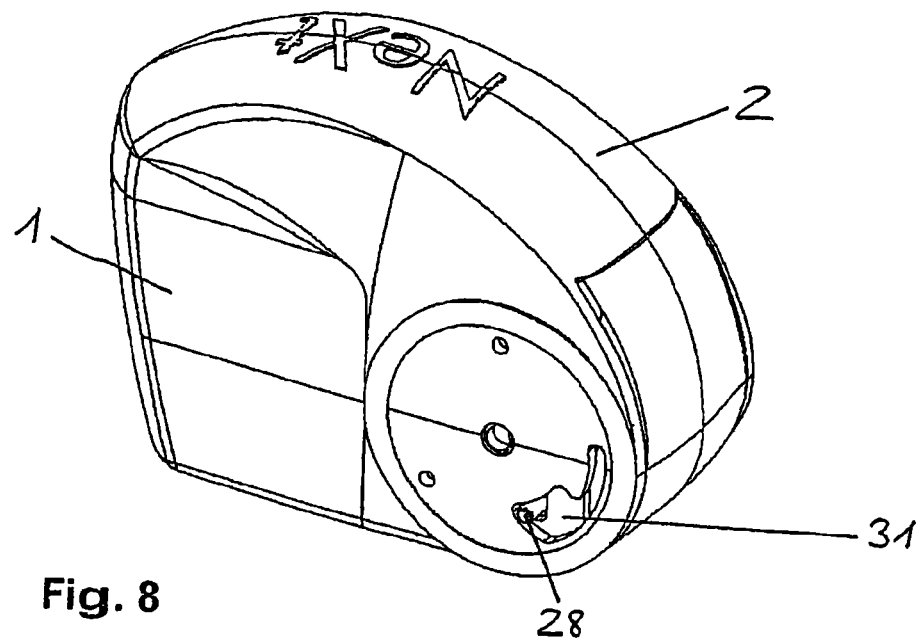
FIG. 8 shows a perspective side view of the powder inhaler without side labels when the cover is closed.

In FIG. 7A and FIG. 7B partial cross-sectional views of the whole powder inhaler along different cross-sectional lines with the cover 2 being dosed are shown. In particular, from FIG. 7A it can be seen that the mouthpiece 3 comprises the inhalation channel 27 extending from the upper side of the mouthpiece 3 downward so as to be coupled to the deagglomerator arrangement (cyclone) 16 of the dosing sub-assembly 13.

The functionality of the inhalation actuated mechanism as well as the dosing counting unit is as follows.

As shown in FIG. 13, there are formed recesses 30 at both front corner portions of the slide 15. At one of these recesses 30, a prolonged end 34 of the drive spring 23 engages with the slide 15 if the slide 15 is moved forward. By the contact with the slide 15, the drive spring 23 of the inhalation actuated mechanism is tensioned and charged up. A first end 33 of the drive spring 23 rests at a portion 41 of the flap 21 when the drive spring 23 is in its discharged state. Therefore, by charging up the drive spring 23 this reset force exerted by the first end 33 of the drive spring 23 on the flap 21, normally holding the flap 21 in a first horizontal position shown in FIG. 9, is released.

Figure 19A:
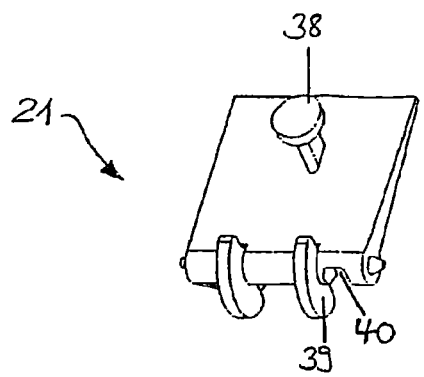
FIGS. 19A, 19B, and 19C show a perspective view, a cross-sectional view, and a front view of an inhalation actuated member of the inhalation actuated mechanism.
Figure 19B:
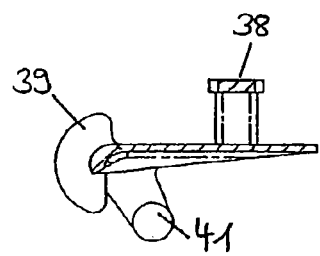
Figure 19C:
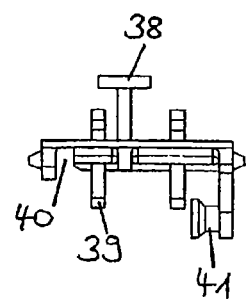

FIGS. 19A, 19B, and 19C show different perspective views of the flap 21. As can be seen, at the upper surface of the flap 21, a flag 38 is formed which acts as a mark being visible through the opening 5 in the mouthpiece 3 when the flap 21 is in its first horizontal position, whereby indicating that a dose is ready for inhalation. Furthermore, the flap 21 comprises a feature 40 for engagement with an arm 43 of the yoke 22. Finally, the flap 21 also comprises two projections 39 which act as a counterweight. This counterweight balances the flap 21 reducing not only the actuation force required but also the susceptibility of the mechanism to accidental triggering.

Figure 9:
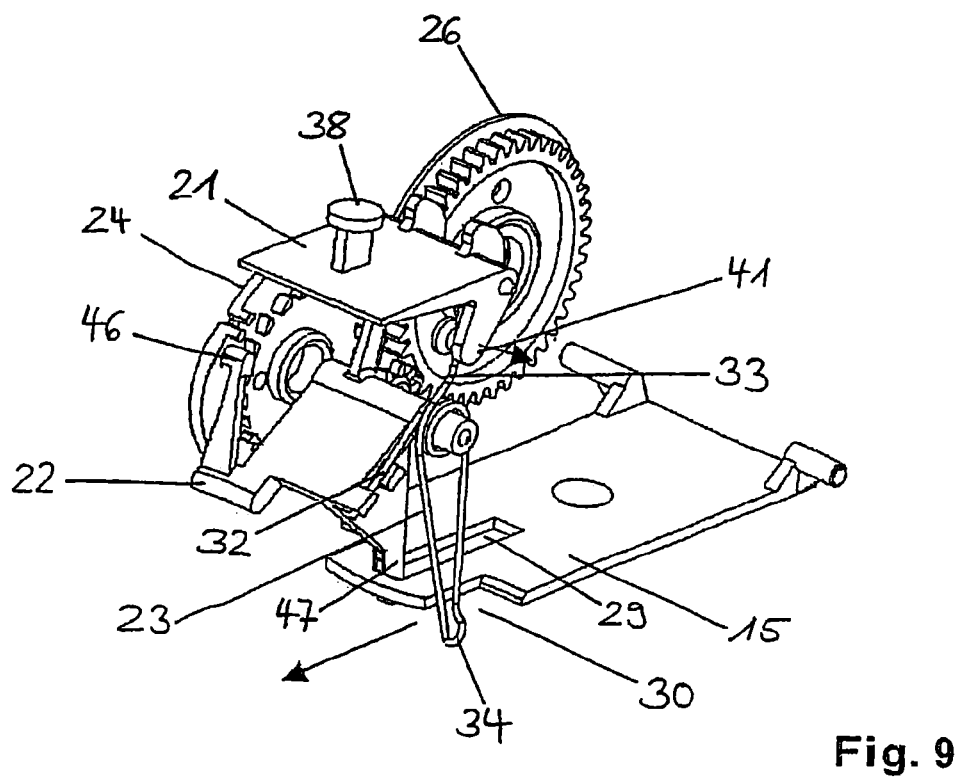
FIG. 9 shows a perspective view of an inhalation (breath) actuated mechanism and a dose counting unit of the powder inhaler.
Figure 21:
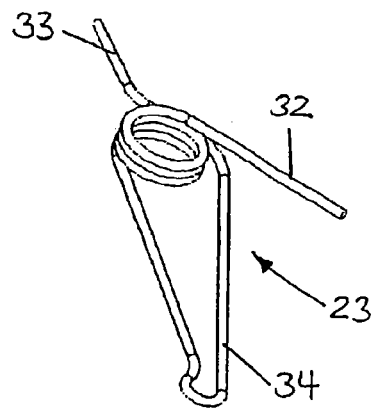
FIG. 21 shows a perspective view of a resilient member of the inhalation actuated mechanism.

As shown in FIGS. 9 and 21, the drive spring 23 has a second end 32 which rests on a lateral side surface 48 of the yoke 22.

Figure 25A:
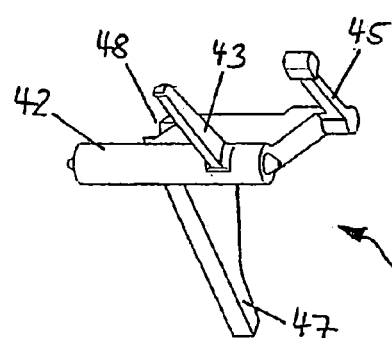
FIGS. 25A and 25B show a perspective view and a side view of a coupling member of the inhalation actuated mechanism and the dose counting unit.
Figure 25B:
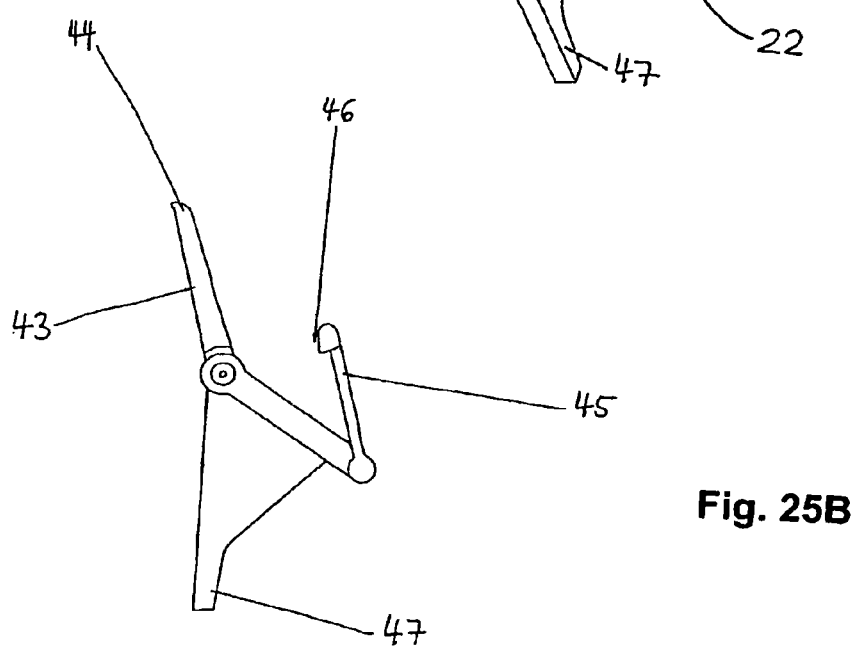

FIGS. 25A and 25B show a perspective view and a side view of the yoke 22. The yoke 22 has a shaft-like portion 42 on which the drive spring 23 is mounted. Furthermore, in FIGS. 25A and 25B the arm 43 is depicted whose upper end 44 is retained and released, respectively, by the flap 21. At that lateral side of the yoke 22 which is opposite to the lateral side surface 48 on which the second end 32 of the drive spring 23 rests, there is formed a projection 45 having a thickening 46 at its end for operating the dose counting unit which will be described later. From the bottom of the yoke 22, there extents a prolongation 47 which engages, on the one hand, with an opening formed in the dose protector 19 and, on the other hand, with a slit 29 formed in the front end portion of the slide 15 (see FIG. 13 and FIG. 20).

As already described above, when the drive spring 23 is decompressed and discharged, its end 33 exerts a reset force on the portion 41 of the flap 21, thereby holding the flap 21 in its first horizontal position, as shown in FIG. 9. In this condition, the dosing protector 19 prevents the powdered medicament contained in the dosing recess 18 from being displaced from the deagglomerator arrangement 16 (cyclone) if the user blows into the mouthpiece 3. Furthermore, the flap 21 provides a resistance if the user blows into the device giving positive feedback.

If, however, the slide 15 is pushed forward by opening the cover 2, thereby compressing and charging the drive spring 23, the reset force exerted by the end 33 of the drive spring on the flap 21 is released, and the flap 21 can be rotated from its first horizontal position shown in FIG. 9 into a second position being pivoted relative to the first position if there is a sufficient high inhalation suction force effected by the user in the inhalation channel 27 of the powder inhaler.

Figure 10:
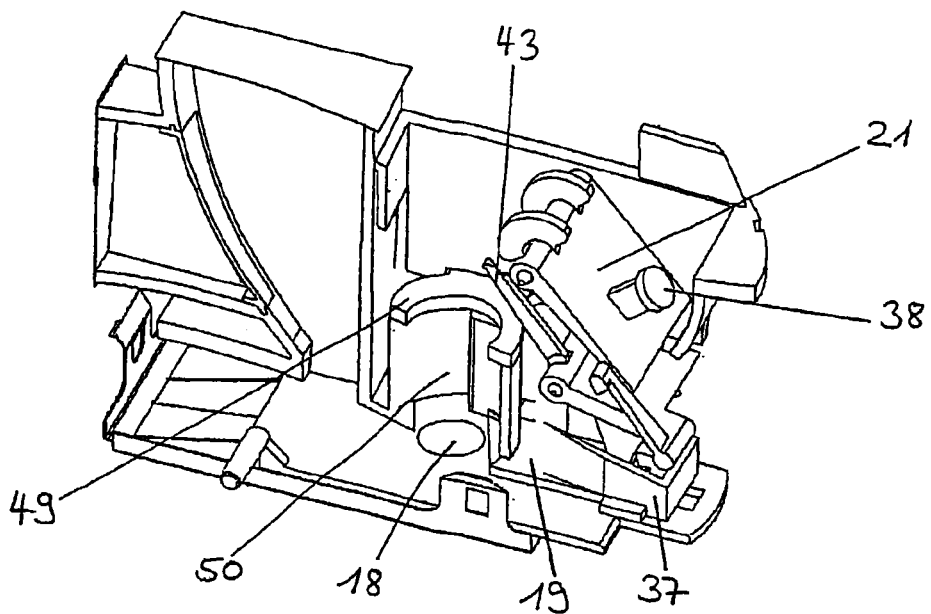
FIG. 10 shows a partial cross-sectional view of the inner construction of the powder inhaler upon inhalation.
Figure 11:
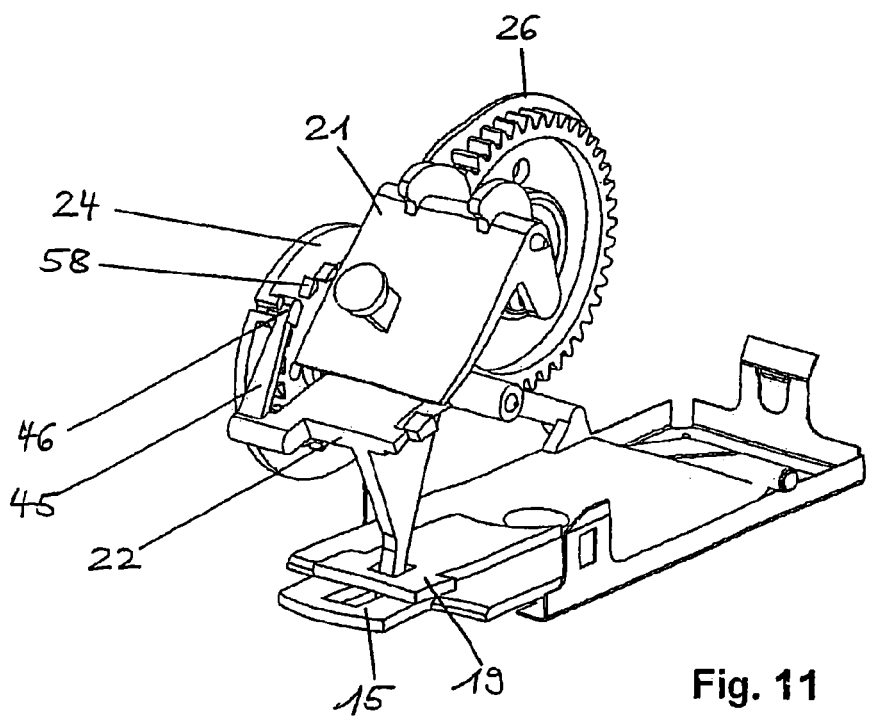
FIG. 11 shows a perspective view of the inhalation actuated mechanism and the dose counting unit of FIG. 9 upon inhalation.

In the latter case, the flap 21 is moved by this sufficient high inhalation force from its first position shown in FIG. 9 into its second position shown in FIG. 10. As can be also seen from FIG. 10, by this movement of the flap 21 the arm 43 of the yoke 22 is released. This enables the drive spring 23, due to its compression, to move its second end 32, which is in engagement with the lateral side surface 48 of the yoke 22, and thus the yoke 22 slightly upward. By this rotational upward movement of the yoke 22 the prolongation 47 extending from the upper side of the yoke 22 is moved forward, thereby moving the dose protector 19 from its closed position to its open position. This situation is shown in FIG. 10 as well as in FIG. 11.

Figure 20:
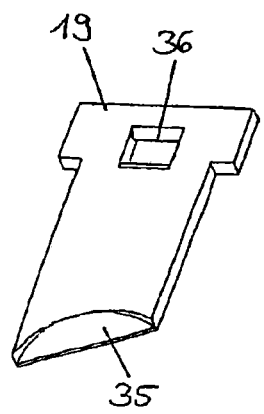
FIG. 20 shows a perspective view of a protective member of the powder inhaler.

In FIG. 20, a perspective view of the dose protector 19 is shown. In particular, in FIG. 20 the opening 36 is shown which is in engagement with the prolongation 47 extending downwardly from the bottom of the yoke 22. The front end 35 of the dose protector 19 has a partial circular or semi-circular shape so that it can form part of the wall of the deagglomerator arrangement or cyclone 16 when the dose protector 19 is in its closed position.

Since the dose protector 19 has been moved out from its closed position into its open position by the yoke 22, the dosing recess 18 of the slide 15 is exposed to the inside 50 of the cyclone, and the dose of the powdered medicament contained in the dosing recess 18 can be inhaled through the cyclone and the inhalation channel 27 as well as the mouthpiece 3. In the cyclone, the drug or the powdered medicament is entrained into a swirling airflow where the active part of the formulation is disaggregated from the carrier (see reference sign 49).

Furthermore, since the flap 21 has been moved from its first horizontal position (see FIG. 9) to its second position rotated or pivoted relative to its first position (see FIGS. 10 and 11), the flag 38 formed at the upper surface of the flap 21 is no longer visible through the opening 5 in the upper side of the mouthpiece 3. That is the flag 38 has disappeared thereby indicating that a dose has been taken, and a new dose is not ready for inhalation again, yet.

Figure 17:
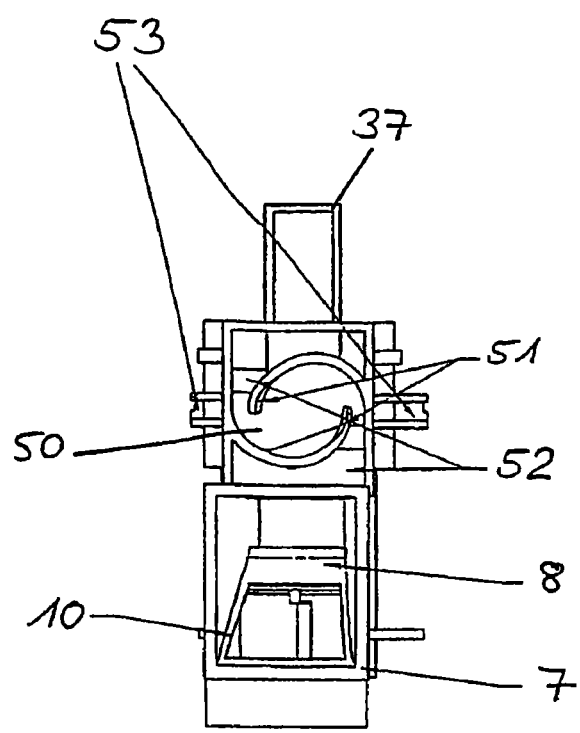
FIG. 17 shows a top view of the dosing sub-assembly shown in FIGS. 6A and 6B.

FIG. 17 shows a top view of the dosing sub-assembly, depicting the inside 50 of the cyclone as well as portions 51 (corresponding to side walls 78 depicted in FIG. 26) which allow the mouthpiece to be assembled, portions 52 which produce a cyclonic airflow within the cyclone, and projections 53 for mounting the dosing sub-assembly within the lower shell 1 of the powder inhaler. Furthermore, in FIG. 17 there is also depicted the end stop 37 for the prolongation 47 of the yoke 22 and the dose protector 19, respectively.

In the following, the functionality of the dose counting unit is explained in detail. As already mentioned above, the dose counting unit, being provided for counting the number of doses taken (up counter) or, alternatively, the number of doses remaining in the container (down counter), comprises the units wheel 24 and the tens wheel 26 being coupled to one another by the idler wheel 25.

FIGS. 22A, 22B, and 22C show a front view, a perspective view, and a rear view of the units wheel 24. The units wheel 24 comprises a central opening 54 at which it is rotatably mounted at the dose counting sub-assembly 14 inside the casing of the powder inhaler as shown in FIGS. 5A and 5B, for example. Reference sign 55 designates a feature which provides a thrust-bearing surface with the lower shell 1. Reference sign 56 designates numbers which are printed on the outer surface of the units wheel 24 along the circumferential direction thereof and with equal intervals therebetween. At the outer periphery of the units wheel 24, there are formed teeth 57 for driving the idler wheel 25. As can be taken from the rear view of the units wheel 24, these teeth 57 are formed diametrically opposed to each other. Finally, on the back of the units wheel 24 there are drive teeth 58 which are brought into engagement with the projection or cantilever 45 of the yoke 22 so as to drive the units wheel 24 step by step upon completion of an inhalation process. As can be easily seen from FIG. 22A C, the drive teeth 58 each are inclined in the circumferential direction of the units wheel 24. For example, the diameter 59 of the units wheel 24 may be about 20 mm.

FIGS. 23A, 23B, and 23C show a rear view, a perspective view and a front view of the tens wheel 26. On the back of the tens wheel 26, there is formed a plurality of teeth 62 in the circumferential direction of the tens wheel 26. These teeth 62 are driven by the idler wheel 25. Reference numeral 60 designates missing teeth which prevent a drive of the tens wheel 26 when the medicament chamber 8 is empty, that is the tens wheel 26 is constructed such that during one life cycle of the powder inhaler nearly one complete rotation of the tens wheel 26 is effected by the dose counting unit. Reference numeral 61 designates an end stop with the casing of the powder inhaler. The diameter 63 of the tens wheel 26, for example, may be about 25 mm. Reference numeral 64 designates an opening at which the tens wheel 26 is rotatably mounted at the dose counting sub-assembly 14, as shown in FIGS. 5A and 5B, for example. Reference numeral 65 designates a feature which provides a thrust-bearing surface with the casing of the powder inhaler. Furthermore, reference numeral 66 designates a feature which provides a thrust-bearing surface with the lower shell 1, and reference numeral 67 designates the periphery of the opening 64 which is located on the casing of the powder inhaler. On the outer surface of the tens wheel 26, there are formed two circumferential rows of numbers 68. These two rows of numbers display tens and hundreds numbers in correct orientation. In each case, a combination of a units number of the units wheel 24 with a tens number and a hundreds number of the tens wheel 26 is visible through the opening 4 formed in the lower shell 1 of the powder inhaler (see FIG. 1, for example). Each such combination of horizontally adjacent numbers of the units wheel 24 and the tens wheel 26 designates a corresponding number of doses remaining in the medicament chamber 8. Finally, at the outer periphery of the tens wheel 26, there is also formed a projection 69. Along the radial direction of this projection 69, there are no tens and hundreds numbers formed on the outer surface of the tens wheel 26, and this projection 69 covers the units wheel 24 if the medicament chamber 8 is empty such that no numbers are visible through the opening 4 of the lower shell 1, thereby indicating to the user that there is no dose remaining in the medicament chamber any more.

Figure 24:
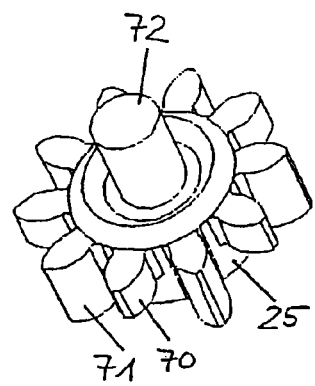
FIG. 24 shows a perspective view of an idler wheel of the dose counting unit.

FIG. 24 shows a perspective view of the idler wheel 25. The idler wheel 25 has a shaft 72 at which it is rotatably mounted on the sub-frame 20 of the dose counting sub-assembly 14 as shown in FIGS. 5A and 5B, for example. Furthermore, the idler wheel 25 has half-width teeth 70 which engage with the drive teeth 57 on the back of the units wheel 24. Furthermore, the idler wheel 25 comprises full width teeth 71 which lock against the units wheel 24. When the units wheel 24 is set to numbers "1" "9" (reference numeral 56 in FIGS. 22A, 22B, and 22C), the teeth 57 on the back of the units wheel 24 fit between the full-width teeth 71 of the idler wheel 25. When the units wheel 24 is set to number "0", however, the teeth 57 engage with the half-width teeth 70.

As has been explained above, the coupling between the units wheel 24 and the tens wheel 26 is such that after each ten step-wise rotations of the units wheel 24 the tens wheel 26 is rotated by one step, thereby increasing the combination of tens and hundreds numbers on the outer surface of the units wheel 24. It should be noted that FIG. 5A shows a situation in which no numbers of the units wheel 24 and the tens wheel 26 are visible through the opening 4 of the lower shell 1, since the projection 69 of the tens wheel 26 covers the respective number of the units wheel 24 so as to indicate that the medicament chamber 8 is empty.

As described above, when the flap 21 is rotated from its horizontal first position to its second position upon an inhalation process initiated by the user (see FIG. 11), the yoke 22 is slightly rotated clockwise (in FIG. 11) so that the dose protector 19 is moved from its closed position to its open position. Furthermore, by this clockwise rotation of the yoke 22, the projection or cantilever 45 of the yoke 22 is also slightly moved clockwise along the inclination of the next drive tooth 58 of the units wheel 24 so as to bring the thickening 46 of the cantilever 45 into engagement with the respective drive tooth 58. Up to this point, no actuation of the units wheel 24 and the tens wheel 26 has taken place.

After inhalation, the user closes the cover 2 of the powder inhaler. With the closing of the cover 2, the slide 15 is moved backward from its inhalation position to its filling position by means of the coupling between the projections 28 of the slide 15 and the profiled cam tracks 31 of the cover 2.

Figure 12:
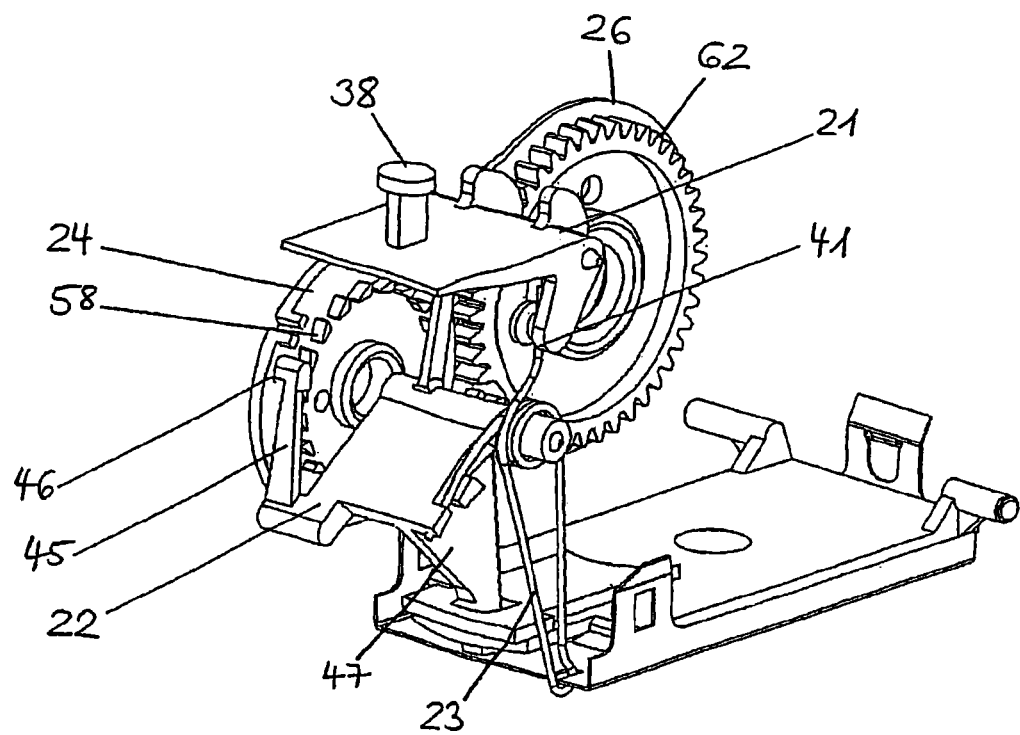
FIG. 12 shows a perspective view of the inhalation actuated mechanism and the dose counting unit of FIG. 9 after closing the cover of the powder inhaler.

As shown in FIG. 12, this backward movement of the slide 15 causes a counter clockwise rotation (as regards the view depicted in FIG. 12) of the yoke 22, since the prolongation 47 of the yoke 22 is moved together with the slide 15 backward. The counter clockwise rotation of the yoke 22 is supported by the drive spring 23 which is allowed to be discharged and decompressed upon backward movement of the slide 15. Due to this counter clockwise rotation of the yoke 22, the cantilever 45 is also rotated counter clockwise, thereby also rotating the units wheel 24 counter clockwise by one step (as regards the view depicted in FIG. 12) which results in decreasing the number of doses left in the medicament chamber 8, which is visible through the opening fear of the lower shell 1. As a matter of course, the dose counting unit can also be arranged such that it does not display the number of doses remaining in the medicament chamber 8, but the number of doses already taken by the user.

Furthermore, since the yoke 22 and the drive spring 23 are moved back into their initial positions, the end 33 of the drive spring 23 urges the flap 21 back into its horizontal first position (as shown in FIG. 12), thereby resetting the flag 38. Moreover, in this situation, the yoke 22 is again held by the engagement of its arm 43 with the feature 40 of the flap 21. Thus, the whole powder inhaler has been transferred into its initial position again.

Another advantage associated with the flag 38 is that it may be pushed down by fingers of a user so as to affect a manual override of the inhalation actuated mechanism. This would enable the user to take the dose if the user is not able to generate a sufficient force in order to actuate the inhalation actuated mechanism.

On completely closing the cover 2, there will be an audible click signaling that the cover is closed. Preferably, the powder inhaler will require the cover 2 to be completely closed to function correctly.

Finally, the deagglomerator arrangement 16 (cyclone) of the powder inhaler should be briefly discussed.

The purpose of this deagglomerator arrangement is to produce clearly defined turbulences within the inhalation channel 27 so as to pulverize agglomerations of the medicament. By the swirling airflow within the deagglomerator arrangement 16, the active part of the formulation is disaggregated from the respective carrier.

In principle the deagglomerator arrangement of the present invention comprises a rotationally symmetrical vortex chamber, at least one substantially tangential air inlet, and an outlet or exit for outputting the air with the deagglomerated powdered medicament, the outlet being spaced from the air inlet in the longitudinal axial direction of the vortex chamber. The general structure of the deagglomerator arrangement, for example, can be taken from FIG. 6A, FIG. 6B, FIG. 7A, and FIG. 17.

In addition, the structure of the deagglomerator arrangement, which is generally not restricted to the usage in powder inhalers as described in connection with the above drawings, will be explained in detail by reference to FIG. 26 and FIG. 27, respectively.

Figure 26:
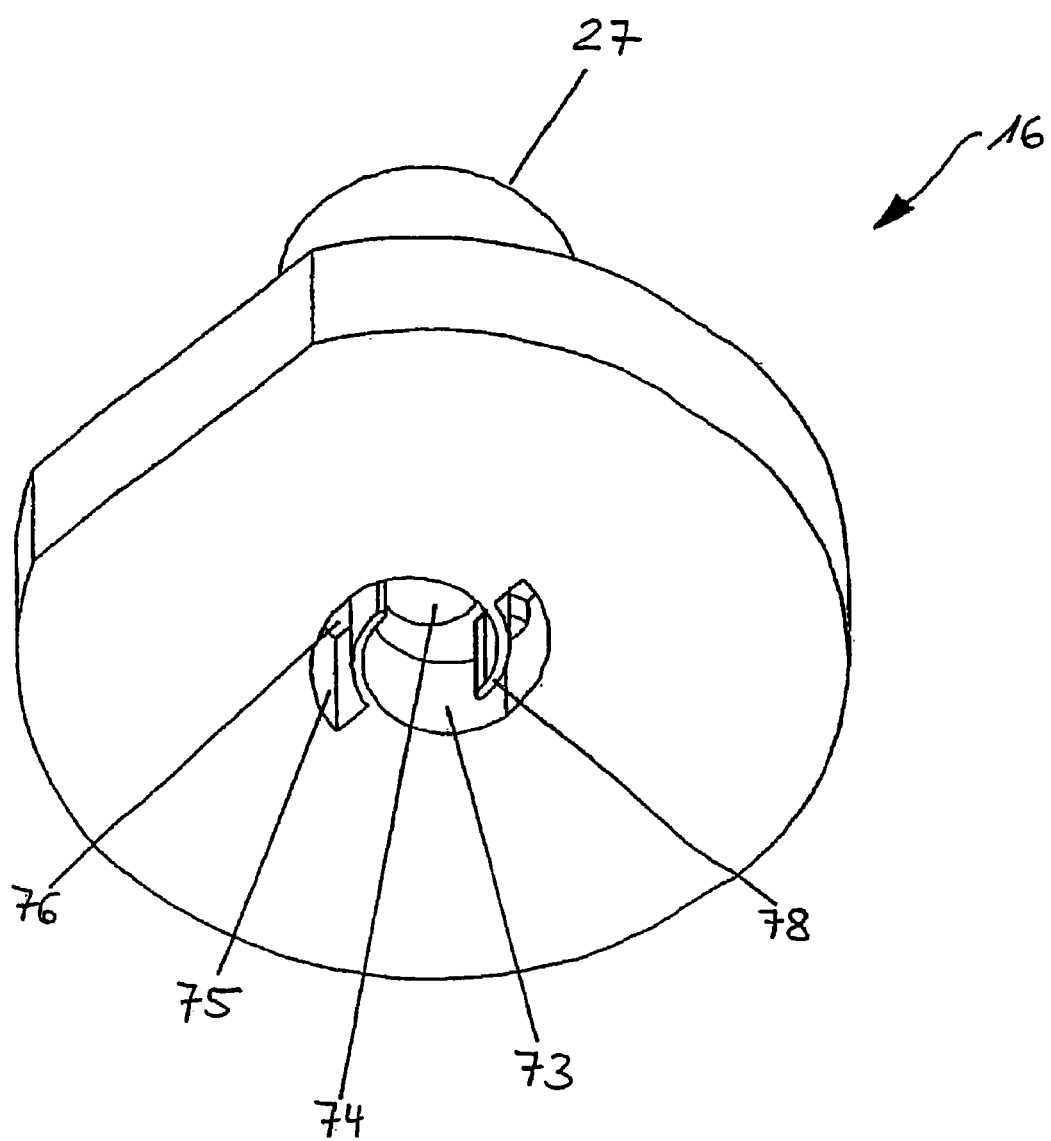
FIG. 26 shows a perspective and schematic bottom view of a deagglomerator arrangement (cyclone).

FIG. 26 shows a schematic perspective view of the deagglomerator arrangement (cyclone) according to a preferred embodiment, the deagglomerator arrangement being constructed to produce a very strong cyclonic flow within the deagglomerator arrangement resulting in a very strong velocity gradient. It is to be noted that FIG. 26 is a schematic view to explain the design and the key features of the cyclone according to the preferred embodiment, but FIG. 26 does not show the cyclone exactly as it is implemented in the above described powder inhaler. The implementation of the cyclone in the powder inhaler, for example, can be taken from FIG. 4 or FIG. 17.

As can be taken from FIG. 26, the deagglomerator arrangement 16 has an opening in its bottom which disembogues into a vortex chamber 73. The vortex chamber 73 is designed substantially rotationally symmetrical. In addition, there are two air inlets (conduits) 75 which direct air substantially tangentially into the vortex chamber 73. As can be seen from FIG. 26, air inlet windows 76 are formed in the upper surface of the air inlet conduits 75 which for example cover 80° of the air inlet conduits 75 so as to enable entry of air from above into the air inlet conduits 75. The base section of the vortex chamber 73, in general, has an elliptical cross-section. As depicted in FIG. 26, there is an outlet 74 formed in the upper end of the vortex chamber 73, the outlet 74 being spaced from the opening for the supply of the powdered medicament and both air inlets in the longitudinal axial direction of the vortex chamber 73. In particular, the outlet 74 is aligned coaxially to the longitudinal central axis of the vortex chamber 73 and extends along this longitudinal central axis. In particular, the outlet 74 has a substantially circular cross-section, the diameter of this circular cross-section being smaller than the diameter of the elliptical cross-section of the vortex chamber 73.

Figure 27:
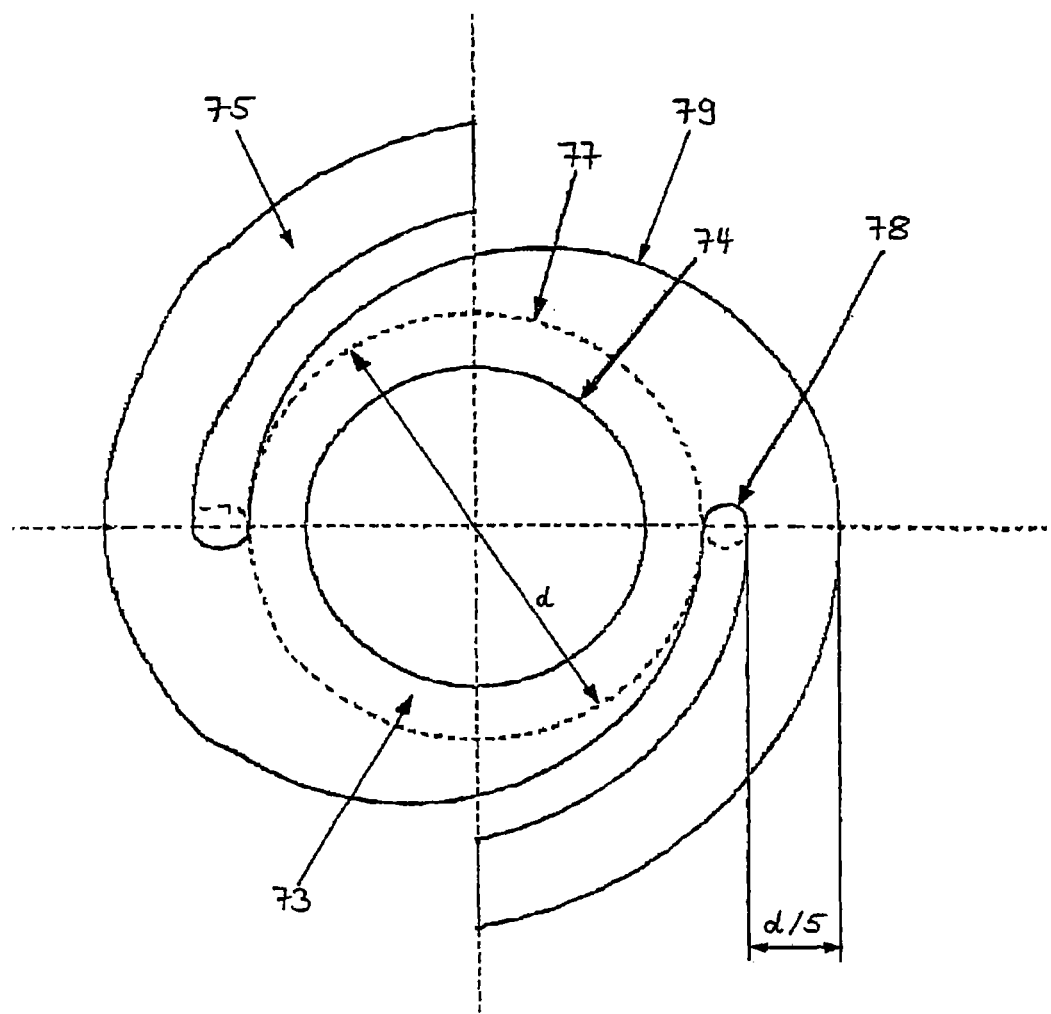
FIG. 27 shows a cross-sectional view of the deagglomerator arrangement of FIG. 26.

FIG. 27 shows a cross-sectional view of the deagglomerator arrangement in accordance with a sectional plane which horizontally intersects the deagglomerator arrangement 16 and the vortex chamber 73, respectively. The view depicted in FIG. 27 could be regarded as a bottom view of the deagglomerator arrangement 16 as well.

In FIG. 27, the vortex chamber 73 and the circular outlet 74, which disembogues into the inhalation channel 27, are depicted. Although the horizontal cross-section of the base section of the vortex chamber 73 has a substantially elliptical shape, the cross-section of the base section of the vortex chamber 73 can also be defined by an imaginary circle which can be laid inside the base section of the vortex chamber 73 on a horizontal plane intersecting both air inlet conduits 75 such that the circumference or periphery of this circle just touches the inside surfaces of both side walls 78 at places which are diametrically opposed to one another without extending beyond the side walls of the vortex chamber 73. In particular, these diametrically opposed places of the side walls 78 are those places of the side-walls 78 where both air inlets of the air inlet conduits 75 disembogue into the vortex chamber 73. In FIG. 27, the respective "base" circle is depicted with a dotted line and assigned with reference numeral 77. The air inlets are arranged along the circumference of the "base" circle 77.

Studies have shown that the diameter d of this "base" circle 77 has an important influence on the deagglomerator effect of the cyclone. For example, if the diameter d is too small, the flow resistance is too high. On the other hand, if the diameter d is too large, the flow resistance is too small resulting only in a minor improvement of the efficiency of the deagglomerator arrangement 16.

Comprehensive studies of the geometry of the deagglomerator arrangement 16 in terms of the flow resistance of the device and the quality of the cyclonic flow effected inside the vortex chamber 73 show that a very good efficiency of the device can be obtained if the diameter d is between 6 mm and 10 mm, preferably 6 mm≤d≤8 mm.

For example, if d is 6 mm, a flow rate of 30 l/min at a pressure of 4 kPa can be obtained. The cyclonic flow inside the vortex chamber 73 is of good quality. Nevertheless, the required increase in the width of the air inlets or in the outlet diameter to allow a higher target flow rate (for example 60 l/min at 4 kPa) would presumably result in a degradation of the quality of the cyclone. This is because the dimensions of the air inlets or of the outlet would be too large in comparison to the dimensions of the main section of the cyclone, which are the dimensions of the vortex chamber 73.

Therefore, it may be recommendable to use a larger diameter d of the "base" circle 77. A very compact design of the cyclone 16 and, in addition, the above-mentioned target flow rate in the range of 60 l/min at 4 kPa can be obtained if the diameter d of the "base" circle 77 is in the range of 8 mm. Larger diameters d of the "base" circle 77 do not lead to further significant improvements of the flow pattern inside the vortex chamber 73 over that which can be achieved with a diameter d=8 mm. Therefore, the diameter d=8 mm is considered as a preferred embodiment of the cyclone 16.

As depicted in FIG. 27, the deagglomerator arrangement or cyclone 16 according to this embodiment has two air inlets assigned with the respective air inlet conduits 75. Both air inlets disemboguing into the vortex chamber 73 are arranged diametrically opposed to one another and preferably have a width or a diameter of d/5. As shown in FIGS. 26 and 27, the side walls 78 separating the air inlet conduits 75 from the vortex chamber 73 end in a fillet which may have an end radius of 0.3 mm, for example. The side walls 78 may have a thickness of 0.6 mm, for example.

The cross-sectional structure of the deagglomerator arrangement 16 is such that a respective semicircle or arc (arched wall) 79, whose center is on the diameter connecting both air inlets or both end portions of the side walls 78, connects the outer wall of one air inlet 75 with the inner surface of the opposing side wall 78 of the vortex chamber 73 at a place where this side wall 78 intersects with the respective other air inlet. As can be seen from FIG. 27, this applies to both outer peripheral portions of the vortex chamber 73 and to both air inlets/air inlet conduits 75, respectively. The side walls of the air inlet conduits 75 are concentric to the side walls 78 of the vortex chamber 73. However, the semicircular or arched (curved) wall portions 79 of the vortex chamber 73 are non-concentric relative to the interior of the vortex chamber 73, i.e. the "base" (horizontal) circle 77. This contributes to a very effective deagglomeration within the vortex chamber 73.

The structure shown in FIG. 27 of the deagglomerator arrangement or cyclone 16 may be extruded over a height of 7.7 mm, for example. The inhalation channel 27, that is the outlet cylinder extending from the circular outlet 74, preferably has a circular diameter of 0.75 d and may be extruded on top of the vortex chamber 73 over a height of 37 mm, for example. The above-mentioned top inlet window 76, covering 80° of the air inlet conduits 75, may be extruded over 2 mm to provide the channels through which the air may enter into the device from the top of these windows.

FIGS. 28A, 28B, and 28C show a perspective view, a bottom view and a top view, respectively, of another embodiment of a dosing sub-assembly 13 of a powder inhaler according to the invention. As can be seen, the container 7 comprises a medicament chamber 8 having an elliptical cross-section. Inside the medicament chamber 8, side walls 80 tapering or being slanted downward are provided, thereby facilitating the filling of the dosing recess of the slide, when it is in its filling position, by gravity. Again, the desiccant chamber 9 is separated from the medicament chamber 8 by a permeable membrane 10.

The dosing sub-assembly 13 of this embodiment comprises a deagglomerator arrangement (cyclone) 16 similar to that described above. From FIG. 28C, the wall portions 79 being non-concentric to the interior diameter of the vortex chamber 73 are evident. Furthermore, FIG. 28C also shows the tangential air inlet conduits 75.

Other features of the invention will become apparent in the course of the following descriptions of exemplary embodiments which are given for illustration of the invention and are not intended to be limiting thereof.

EXAMPLES

The primary objective of this example is to assess the inspiratory flow profile through the device disclosed in EP 1 386 630 in adult asthmatics with varying degrees of disease control.

1. Study Design.

This study is a phase IIa, single-center, open-label, single-arm study, to evaluate the inspiration profile through the device disclosed in EP 1 386 630 (hereinafter the Device) in adult asthmatic patients with varying degrees of disease control.

If the subjects meet the inclusion/exclusion criteria, they will be instructed to use the Device. The patients will subsequently inhale through the Device and the inspiration profile will be measured.

2. Subject Selection Criteria.

2.1 Subject Recruitment.

A total of 40 asthmatic adults (≥18 years), 20 with controlled stable disease and 20 with partly controlled or uncontrolled disease according to GINA guidelines (2011), will be enrolled. 44 patients will be screened in order to have 40 patients completed (assuming a screening failure rate of 10%).

2.2 Inclusion Criteria.

Patients will be enrolled at clinic if all the following criteria are satisfied:

1. Written informed consent obtained from the patient or the legal representatives.
2. Inpatients and outpatients of both sexes, aged ≥18 years.
3. Clinical diagnosis of controlled, partly controlled or uncontrolled asthma according to GINA guidelines (2011).
4. A cooperative attitude and ability to use DPIs and to be trained in the proper use of the Device as confirmed by the activation of the training device BAM.

2.3 Exclusion Criteria.

Patients will not be enrolled if one or more of the following criteria are present:

1. Pregnant women confirmed by a positive urinary β-HCG laboratory test (>5 IU/ml) or nursing (lactating) women (if applicable).
2. Significant seasonal variation in asthma or asthma occurring only during episodic exposure to an allergen or a chemical sensitizer.
3. History of near fatal asthma (e.g. brittle asthma, hospitalisation for asthma exacerbation in Intensive Care Unit).
4. Diagnosis of restrictive lung disease.
5. Allergy to any component of the placebo treatment.
6. Inability to comply with study procedures or treatment.
7. Significant unstable medical history of and/or treatments for cardiac, renal, neurological, hepatic, endocrine diseases, or any laboratory abnormality indicative of a significant underlying condition, that may interfere with patient's safety, compliance, or study evaluations, according to the investigator's opinion.

2.4 Subject Withdrawals.

Patients have the right to withdraw from the study at any time for any reason, including personal reasons. The investigator also has the right to withdraw patients from the study in the event of:

1. Non-compliance with the protocol and/or lack of willingness or commitment to co-operate in all phases of the study.
2. Protocol deviations.
3. Adverse event which is considered intolerable by the patient or the investigator.
4. Development of an exclusion criterion.

3. Dosage and Administration.

3.1 Dosage.

At the study visit all patients will receive 2 inhalations of Placebo filled in the Device.

3.2 Administration.

The administration of the device containing placebo will take place in the morning at clinic visit under medical supervision. The training with an empty Device will be performed by a physician during the visit at clinic.

4. Study Plan.

4.1. Study Schedule.

The study plan foresees one visit at clinic.

Visit 1:

1. Written informed consent will be obtained from the patient or the legal representatives.
2. The patient's eligibility for entry into the study will be assessed according to the inclusion and exclusion criteria.
3. A pregnancy test (urinary β-HCG) will be done in females of child-bearing potential.
4. Medical history will be recorded and a full physical examination will be performed.
5. Vital signs will be measured, after 10 minutes of rest, in sitting position: heart rate (HR), systolic (SBP) and diastolic (DBP) blood pressure.
6. A spirometry assessment will be performed.
7. The patient will be successfully trained in the proper use of the Device as confirmed by the activation of the training device BAM.
8. The Device containing placebo will be dispensed to the patient. The use of the device is taken on site under the investigator's supervision, verifying the appropriate inhalation.
9. Recording of inhalation profile through acoustic monitoring will be performed during two consecutive maneuvers (inhalations), separated by a maximum of 3 minutes. If a maneuver will be judged as unacceptable by the investigator, additional maneuvers and inhalation profile recordings may be performed. The reason for performing any additional maneuver should be recorded by the investigator. Unless a valid justification will be provided, the first two maneuvers following investigator's instructions will be considered in the analysis. Generally, a poor maneuver by the patient will not be considered as a valid reason for performing additional recordings of inhalation profile. Additional maneuvers in case of technical issues (for example a disconnection of the audio jack during the inhalation) are acceptable.
10. Device usability evaluation assessed by the Investigator by means of a questionnaire.

Any adverse events occurring since the signature of the informed consent will be recorded.

4.2. Investigations.

4.2.1. Spirometry at clinic.

A computer-operated pneumotachographic spirometer will be used for all respiratory function measurements at the clinic visit. Lung function measurements and daily calibration of the spirometer will be done according to the recommendation of the Official Statement of the European Respiratory Society and American Thoracic Society (Miller M R, et al. Standardisation of spirometry Eur Respir J 2005; 26: 319-38, which is incorporated herein by reference in its entirety).

Lung function measurements will be done with patients either standing or sitting (for each patient, this should be consistent throughout the study) with the nose clipped after at least 10 minutes rest. Calibration of the spirometer must be performed by the same investigator at each visit prior to spirometry manoeuvres and the reports must be kept with the source study documents.

The lung function measurement will start in the morning at 8:00-11:00 a.m., approximately at the same time of the day for each patient.

The following parameters will be assessed at each visit:

1. Forced Expiratory Volume in the $1^{st}$ second ($FEV_1$, L and % predicted).
2. Forced Vital Capacity (FVC, L and % predicted).
3. Peak Expiratory Flow (PEF, L/min and % predicted).
4. Peak Inspiratory Flow (PIF, L/min).

Spirometry will be performed at clinic visit to evaluate asthma control as per GINA 2011 guidelines and shown in Table 1.

TABLE 1

Assessment of Current Clinical Control.

| Characteristics | Controlled (All of the following) | Partly Controlled (Any measure present) | Uncontrolled |
| --- | --- | --- | --- |
| Daytime symptoms | None (twice or less/week) | More than twice/week | Three or more features of partly controlled asthma |
| Limitation of activities | None | Any | |
| Nocturnal symptoms/awakening | None | Any | |
| Need for reliever/rescue treatment | None (twice or less/week) | More than twice/week | |
| Lung Function (PEF or $FEV_1$) | Normal | <80% predicted or personal best (if known) | |

Predicted values will be calculated according to the formulas reported by Quanjer et al. (Quanjer P H, et al. Spirometric reference values for white European children and adolescents: Polgar revisited Pediatr Pulmonol 1995; 19: 135-42; Quanjer P H. Lung volumes and forced ventilatory flows Eur Respir J 1993; 6 suppl 16: 5-40, which are incorporated herein by reference in their entireties).

For $FEV_1$, FVC, PEF, and PIF the highest value from three technically satisfactory attempts will be considered (irrespective of the curve they come from). The chosen value should not exceed the next one by more than 200 ml (FEV1). If the difference is larger, up to 8 measurements will be made and the largest value be reported.

4.2.2. Measurement of Inspiratory Flow Profile by Acoustic Monitoring.

Assessment of inspiratory profile through the Device will be performed according to a technology, disclosed in WO 2011/135353 (which is incorporated herein by reference in its entirety), that monitors and measures key performance characteristics of an inhaler (pMDI, DPI, or nebulizer) providing valuable feedback to the user, clinician, or healthcare provider thereby promoting correct usage. Said technology is based on the use of an acoustic analysis to accurately measure the key performance characteristics during the inspiratory manoeuvre such as flow at and time to BAM firing, flow at and time to powder ejection, PIF and time to PIF, initial acceleration, total inhaled volume and inhalation time.

All the parameters will be automatically calculated by the software.

4.2.3. Vital Signs.

Systolic and diastolic blood pressure (SBP, DBP) and heart rate (HR) will be measured at pre-dose after 10 min rest in sitting position.

5. Assessments.

5.1. Variables Measured by Acoustic Monitoring Technology Through the Device During the Inspiratory Maneuver:
 1. inspiratory flow rate by time;
 2. flow at and time to BAM firing;
 3. peak inspiratory flow (PIF) and time to PIF;
 4. initial acceleration (rate of change of flow at inhalation start);
 5. total inhaled volume and inhalation time;
 6. flow and time to powder ejection (if feasible).

5.2. Pulmonary Function by Spirometry: $FEV_1$, $FEV_1$ Percent of Predicted Normal Value, FVC, FVC percent of predicted normal value, PEF, PEF percent of predicted normal value and PIF.

5.3. Device Usability by Means of a Physician-Assessed Questionnaire.

6. Safety Assessments.

Adverse events.

7. Results and Discussion.

During inhalation maneuvers, it is important that patients generate a turbulent energy inside the device in order to promote the de-aggregation of the powder and an effective release and delivery of the dose. This turbulent energy is the result of the inspiratory flow generated by the patient and the internal resistance of the device and corresponds to an overall pressure drop of 4 kPa. Therefore, the inspiratory flows of asthmatic patients is a critical factor in determining the de-aggregation and, hence, the correct delivery of the drug. Different asthmatic patients may be generating different inhalation flows depending on their pulmonary function status. However, it has been known that inhalation flows alone does not provide complete and accurate information about the de-aggregation event, but that the initial acceleration is another critical factor in determining the sequence of events leading to an effective powder release and delivery to the airways. In this study, therefore, the complete inhalation profile through a multi-dose reservoir type BAM activated device in asthmatic patients with different degrees of flow limitations was studied. 40 asthmatic subjects were studied, 20 with controlled and 20 with poorly controlled or uncontrolled asthma as per GINA guidelines of 2011.

Figure 29:
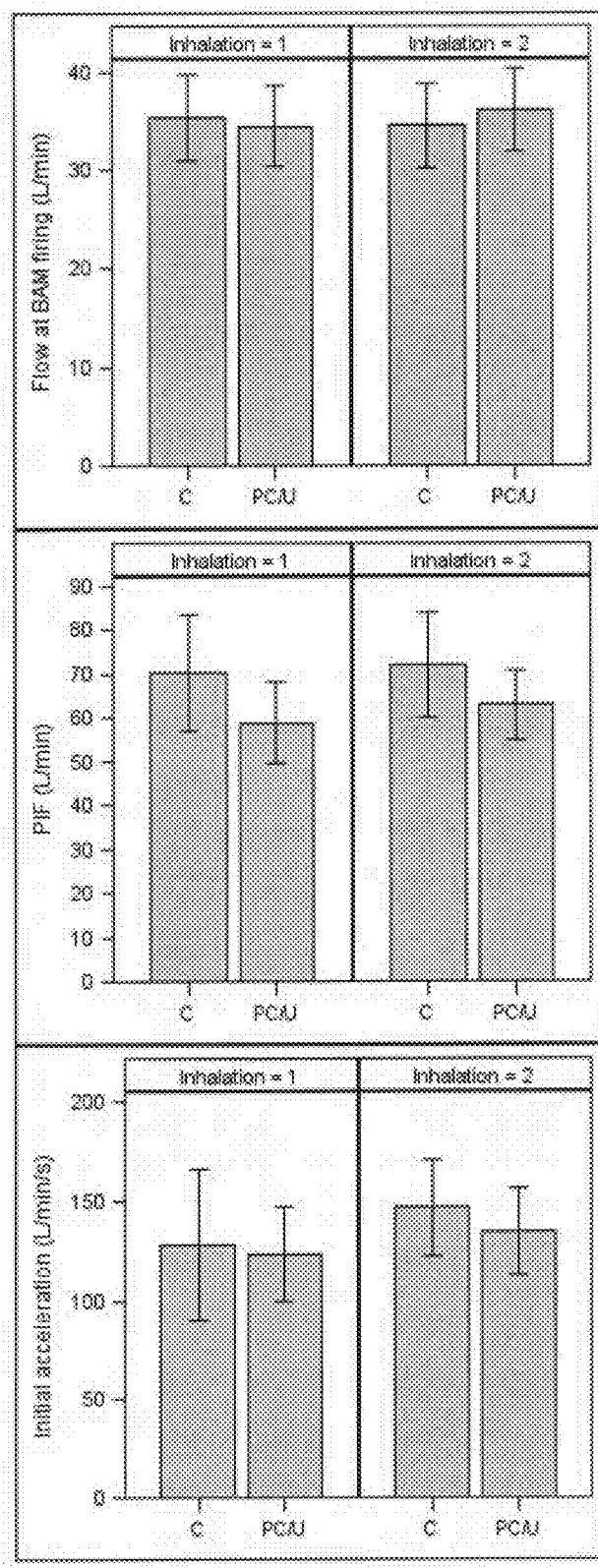
FIG. 29 shows the main parameters defining the flow profile within the device of EP 1 386 630 in controlled (C) and poorly controlled or uncontrolled (PC/U) asthmatic patients. From the top to the bottom: flow at BAM firing, peak inspiratory flow (PIF) and initial acceleration.
Figure 30:
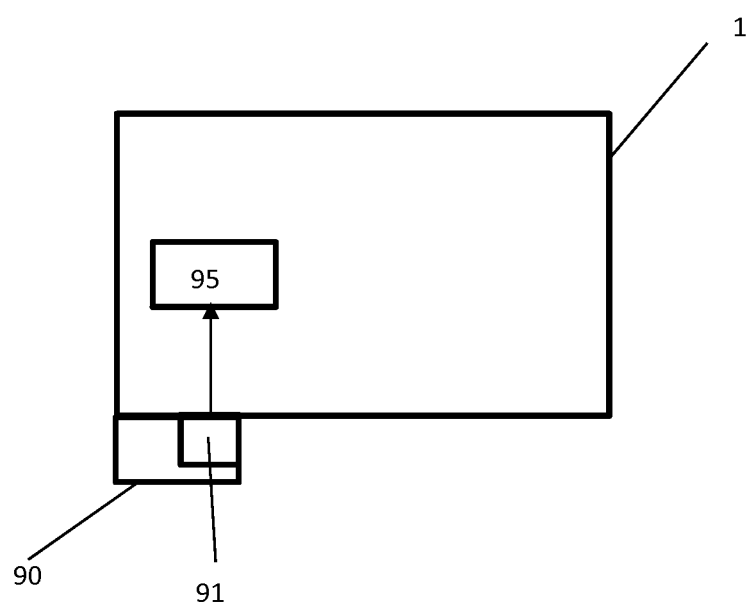
FIG. 30 is a schematic representation of the body and microphone mounted on an external surface of the body according to embodiments of the disclosed subject matter.

The results of this study are illustrated in FIG. 29 and describe the main parameters defining the flow profile within the device of EP 1 386 630 in controlled and poorly controlled or uncontrolled asthmatic patients. In particular the mean (±SD) flow at BAM firing was 35.39 (±9.49) and 34.51 (±8.63) l/min for the first inhalation in controlled (C) and poorly controlled or uncontrolled patients (PC/U) respectively, whereas it was 34.57 (±9.17) and 36.16 (±8.99) l/min for the second inhalation in C and PC/U respectively. The mean (±SD) peak inspiratory flow (PIF) generated inside the device was 70.46 (±28.23) and 58.82 (±20.13) l/min for the first inhalation in C and PC/U patients respectively, whereas for the second inhalation it was 72.10 (±25.62) and 63.04 (±16.83) l/min in C and PC/U patients, respectively. The mean (±SD) initial acceleration was 128.15 (±80.82) and 123.52 (±50.62) L/min/sec for the first inhalation in C and PC/U patients, respectively, whereas for the second inhalation it was 146.58 (±51.92) and 134.40 (±46.70) L/min/sec in C and PC/U patients, respectively.

Collectively, these data showed the complete inhalation profile through the device disclosed in EP 1 386 630. The results of this study suggest that the inhalation flow triggering the activation of the BAM falls within the range defining a high resistance device and that this value is fairly consistent regardless of the type of patient and its functional limitations. There seems to be a lower inhalation flows for PC/U asthmatics compared to C asthmatics (although the sample size is not large enough to reach statistical significance) which, however, appears not to occur at low flow rate and consistently in controlled and poorly controlled or uncontrolled asthmatic patients.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A therapeutic method of treating a patient with at least one respiratory disease, said therapeutic method comprising:
providing a dry powder inhaler having therein a powdered medicament with a formulation comprising (1) a beta-$_2$ agonist, an anti-cholinergic, or a corticosteroid alone or in any combination thereof, and (2) coarse carrier particles of a physiologically acceptable excipient having a mass median diameter higher than 90 microns and a mass diameter between 50 microns and 500 microns; and
administering the powdered medicament using the dry powder inhaler,
wherein the dry powder inhaler includes:
a body, and
a cover,
wherein the body of the dry powder inhaler has:
a container including a medicament chamber for storing the powdered medicament and an integral desiccant chamber for storing a desiccant, the desiccant chamber being separated from the medicament chamber by a permeable membrane,
a metering member having a dosing recess, the metering member being moveable between a filling position, in which the dosing recess is in alignment with an opening of the container so as to be filled with a dose of the powdered medicament, and an inhalation position, in which the dosing recess is in alignment with an inhalation channel,
a mouthpiece in communication with the inhalation channel to enable inhalation of the dose of the powdered medicament contained in the dosing recess of the metering member when the metering member is in the inhalation position,
a protective member, provided between the metering member and the inhalation channel, that is moveable between a closed position, in which the protective member at least covers the dosing recess of the metering member when the metering member is in the inhalation position, thereby preventing the powdered medicament contained in the dosing recess from entering into the inhalation channel and an open position, in which the protective member does not cover the dosing recess, thereby exposing the dosing recess to the inhalation channel so as to enable inhalation of the dose of the powdered medicament contained in the dosing recess,
a breath actuated mechanism (BAM) coupled to the protective member such that, when the protective member is in the closed position, the BAM causes the protective member to move into the open position responsive to an inhalation suction force effected by the patient exceeds a predetermined value, and
the inhalation channel, provided with a deagglomerator system to deagglomerate the powdered medicament, the inhalation channel having a vortex chamber with an opening for the supply of the powdered medicament, two air inlets to direct air tangentially into the vortex chamber, and an outlet to output air with the deagglomerated powdered medicament, the outlet being spaced from the air inlets in an axial direction of the deagglomerator system, an outer wall of each air inlet being connected to the other air inlet by an arched wall portion of the vortex chamber, and each arched wall portion being positioned non-concentric to a horizontal circle defining a diameter of the vortex chamber of 6 mm<d<10 mm, where 'd' is the diameter,
wherein the dry powder inhaler further includes:
a microphone integrated with a preamplifier mounted on an external surface of the body of the dry powder inhaler, and
processing circuitry configured to:
process an acoustic signal, produced in correspondence with airflow through the deagglomerator system, obtained from the microphone,
determine one or more operating conditions of the dry powder inhaler, for use for treatment of the patient affected by the at least one respiratory disease, based on the processed acoustic signal,
(i) track the acoustic signal obtained from the microphone during an inhalation of the patient,
(ii) convert the acoustic signal into a flow inhalation profile using stored first calibration data,
(ii) process the acoustic signal obtained from the microphone to detect firing of the BAM and a timing of delivery of the powdered medicament during the inhalation of the patient,
(iv) compare the detected timing of the delivery of the powdered medicament relative to the flow inhalation profile with stored second calibration data to determine whether the delivery of the powdered medicament meets a desired delivery condition,
enable monitoring, based on (i)(iv), of:
(a) a flow rate profile,
(b) that the BAM did not fire,
(c) that the BAM fired but nothing was delivered, and
(d) that the BAM fired and the powdered medicament was delivered,
wherein the patient is a child younger than 12 years old, and
wherein the at least one respiratory disease includes moderate to severe persistent asthma or severe chronic obstructive pulmonary disease (COPD).

2. The therapeutic method according to claim 1, wherein the cover of the dry powder inhaler is rotatably coupled to the body so that the cover is moveable between a closed position, in which the cover covers the mouthpiece, and an open position, in which the cover exposes the mouthpiece.

3. The therapeutic method according to claim 2, wherein the formulation comprises formoterol fumarate dihydrate and beclometasone dipropionate.

4. The therapeutic method according to claim 2, wherein the body of the dry powder inhaler has a window to display a number of doses of the powdered medicament remaining in the container or having been inhaled, the number of doses of the powdered medicament being counted by a dose counting unit.

5. The therapeutic method according to claim 4, wherein the formulation comprises formoterol fumarate dihydrate and beclometasone dipropionate.

6. The therapeutic method according to claim 2, wherein the body of the dry powder inhaler has an opening to display a mark showing whether the dose of the powdered medicament contained in the dosing recess of the metering member is ready for inhalation, or has already been inhaled.

7. The therapeutic method according to claim 6, wherein the formulation comprises formoterol fumarate dihydrate and beclometasone dipropionate.

8. The therapeutic method according to claim 1, wherein the one or more operating conditions of the dry powder inhaler comprise one or more of an inspiratory flow rate by time, a flow at and time to BAM activation, a peak inspiratory flow (PIF) and time to PIF, an initial acceleration, and a total inhaled air volume.

9. The therapeutic method according to claim 1, wherein the processing circuitry is mounted within the body of the dry powder inhaler.

10. The therapeutic method according to claim 1, wherein the formulation comprises formoterol fumarate dihydrate and beclometasone dipropionate.

11. The therapeutic method according to claim 1, wherein the microphone is a MicroElectrical-Mechanical System (MEMS) microphone.

12. The therapeutic method according to claim 1, wherein the microphone is mounted on a bottom of the external surface of the body of the inhaler.

13. The therapeutic method according to claim 1, further comprising outputting, from the dry powder inhaler, to the processing circuitry, data corresponding to the acoustic signal obtained from the microphone, the processing circuitry processing the data to determine the one or more operating conditions of the dry powder inhaler, for use for treatment of the patient affected by the moderate to severe persistent asthma or the severe COPD, wherein the processing circuitry is remote from the dry powder inhaler.

14. The therapeutic method according to claim 1, further comprising storing, in memory, a count corresponding to a number of times that the BAM is activated and the deagglomerated powdered medicament is successfully delivered, and a second count corresponding to a number of times that the BAM is activated but no deagglomerated powdered medicament is delivered or a suitable amount of the deagglomerated powdered medicament is not delivered, based on data corresponding to each said acoustic signal obtained from the microphone and processed by the processing circuitry.

15. A therapeutic method of treating a patient with at least one respiratory disease, said therapeutic method comprising:
providing a dry powder inhaler having therein a powdered medicament with a formulation comprising (1) a beta-$_2$ agonist, an anti-cholinergic, or a corticosteroid alone or in any combination thereof, and (2) coarse carrier particles of a physiologically acceptable excipient having a mass median diameter higher than 90 microns and a mass diameter between 50 microns and 500 microns;
administering the powdered medicament using the dry powder inhaler,
wherein the dry powder inhaler includes:
a body, and
a cover,
wherein the body of the dry powder inhaler has:
a container including a medicament chamber for storing the powdered medicament and an integral desiccant chamber for storing a desiccant, the desiccant chamber being separated from the medicament chamber by a permeable membrane,
a metering member having a dosing recess, the metering member being moveable between a filling position, in which the dosing recess is in alignment with an opening of the container so as to be filled with a dose of the powdered medicament, and an inhalation position, in which the dosing recess is in alignment with an inhalation channel,
a mouthpiece in communication with the inhalation channel to enable inhalation of the dose of the powdered medicament contained in the dosing recess of the metering member when the metering member is in the inhalation position,
a protective member, provided between the metering member and the inhalation channel, that is moveable between a closed position, in which the protective member at least covers the dosing recess of the metering member when the metering member is in the inhalation position, thereby preventing the powdered medicament contained in the dosing recess from entering into the inhalation channel and an open position, in which the protective member does not cover the dosing recess, thereby exposing the dosing recess to the inhalation channel so as to enable inhalation of the dose of the powdered medicament contained in the dosing recess,
a breath actuated mechanism (BAM) coupled to the protective member such that, when the protective member is in the closed position, the BAM causes the protective member to move into the open position responsive to an inhalation suction force effected by the patient exceeds a predetermined value, and
the inhalation channel, provided with a deagglomerator system to deagglomerate the powdered medicament, the inhalation channel having a vortex chamber with an opening for the supply of the powdered medicament, two air inlets to direct air tangentially into the vortex chamber, and an outlet to output air with the deagglomerated powdered medicament, the outlet being spaced from the air inlets in an axial direction of the deagglomerator system, an outer wall of each air inlet being connected to the other air inlet by an arched wall portion of the vortex chamber, and each arched wall portion being positioned non-concentric to a horizontal circle defining a diameter of the vortex chamber of 6 mm<d<10 mm, where 'd' is the diameter,
wherein the dry powder inhaler further includes:
a microphone integrated with a preamplifier mounted on an external surface of the body of the dry powder inhaler, and
processing circuitry operable to process an acoustic signal produced in correspondence with airflow through the deagglomerator system, obtained from the microphone, to determine one or more operating conditions of the dry powder inhaler, for use for treatment of the patient affected by the at least one respiratory disease,
wherein the at least one respiratory disease includes moderate to severe persistent asthma or severe chronic obstructive pulmonary disease (COPD), and
wherein the formulation comprises formoterol fumarate dihydrate and beclometasone dipropionate;
outputting, from the dry powder inhaler, to the processing circuitry, data corresponding to the acoustic signal, wherein the processing circuitry is remote from the dry powder inhaler;
processing, using the processing circuitry, the acoustic signal;

determining, using the processing circuitry, the one or more operating conditions of the dry powder inhaler, for use for treatment of the patient affected by the moderate to severe persistent asthma or the severe COPD based on the processed acoustic signal;
(i) tracking, using the processing circuitry, the acoustic signal obtained from the microphone during an inhalation of the patient,
(ii) converting, using the processing circuitry, the acoustic signal into a flow inhalation profile using stored first calibration data,
(ii) processing, using the processing circuitry, the acoustic signal obtained from the microphone to detect firing of the BAM and a timing of delivery of the powdered medicament during the inhalation of the patient,
(iv) comparing, using the processing circuitry, the detected timing of the delivery of the powdered medicament relative to the flow inhalation profile with stored second calibration data to determine whether the delivery of the powdered medicament meets a desired delivery condition,
monitoring, using the processing circuitry and based on (i)-(iv):
  (a) a flow rate profile,
  (b) that the BAM did not fire,
  (c) that the BAM fired but nothing was delivered, and
  (d) that the BAM fired and the powdered medicament was delivered.

* * * * *